United States Patent
Vailhe et al.

(10) Patent No.: US 11,219,449 B2
(45) Date of Patent: Jan. 11, 2022

(54) SUTURE NEEDLE PACKAGES FOR LOADING SUTURE NEEDLES AND METHODS OF PASSING SUTURE NEEDLES THROUGH TROCARS

(71) Applicant: Ethicon, Inc., Somerville, NJ (US)

(72) Inventors: Christophe Vailhe, Hillsborough, NJ (US); Doug Souls, Andover, NJ (US)

(73) Assignee: Ethicon, Inc., Somerville, NJ (US)

( * ) Notice: Subject to any disclaimer, the term of this patent is extended or adjusted under 35 U.S.C. 154(b) by 74 days.

(21) Appl. No.: 16/282,901

(22) Filed: Feb. 22, 2019

(65) Prior Publication Data

US 2020/0268383 A1    Aug. 27, 2020

(51) Int. Cl.
*A61B 17/06* (2006.01)
*A61B 17/04* (2006.01)
*A61B 17/00* (2006.01)

(52) U.S. Cl.
CPC .... *A61B 17/06133* (2013.01); *A61B 17/0469* (2013.01); *A61B 17/0482* (2013.01);
(Continued)

(58) Field of Classification Search
CPC ............ A61B 17/0483; A61B 17/0491; A61B 17/062; A61B 17/0625; A61B 2017/047; A61B 17/0469; A61B 17/06114; A61B 17/06133; A61B 17/06138; A61B 17/06142; A61B 17/06147
See application file for complete search history.

(56) References Cited

U.S. PATENT DOCUMENTS 3,112,825 A * 12/1963 Hammond ....... A61B 17/06123
  206/63.3
4,123,125 A    10/1978 Andry, III
(Continued)

FOREIGN PATENT DOCUMENTS

EP    1588666 A2    10/2005
EP    1842494       10/2007
EP    2241264 A1    10/2010

OTHER PUBLICATIONS

International Search Report issued in corresponding International Application No. PCT/IB2020/051379, dated Jun. 9, 2020, 8 pages.

*Primary Examiner* — Darwin P Erezo
*Assistant Examiner* — Raihan R Khandker

(57) ABSTRACT

A system for aligning a needle driver with a tip of a suture needle includes a suture needle package having a base, a needle driver alignment guide, and at least one connector for securing the suture needle. The needle driver alignment guide has first and second lateral guide walls that oppose one another for defining a needle driver guide channel. An end wall interconnects the first and second lateral guide walls for defining a distal end of the needle driver alignment guide. The at least one connector secures the suture needle over the base and controls the orientation of the suture needle so that a tip of the suture needle is located within the suture needle guide channel and is bounded by the end wall and the first and second lateral guide walls. A needle driver has a clamping assembly at a distal end that engages the end wall of the needle driver alignment guide for aligning the clamping assembly with the tip of the suture needle.

24 Claims, 29 Drawing Sheets

(52) U.S. Cl.
CPC .................. *A61B 17/06066* (2013.01); *A61B 2017/00867* (2013.01); *A61B 2017/0479* (2013.01); *A61B 2017/0608* (2013.01); *A61B 2017/06142* (2013.01)

(56) References Cited

U.S. PATENT DOCUMENTS

| | | | |
|---|---|---|---|
| D273,615 S | | 4/1984 | Maskrey |
| 5,282,533 A | | 2/1994 | Holzwarth et al. |
| 5,478,344 A | * | 12/1995 | Stone ................ A61B 17/0469 206/339 |
| 5,478,345 A | * | 12/1995 | Stone ................ A61B 17/0469 206/339 |
| 5,503,266 A | | 4/1996 | Kalbfeld |
| 5,655,652 A | | 8/1997 | Sobel et al. |
| 5,788,062 A | * | 8/1998 | Cerwin ............ A61B 17/06133 206/63.3 |
| 5,848,714 A | | 12/1998 | Robson et al. |
| 5,906,273 A | | 5/1999 | Pohle et al. |
| 6,260,696 B1 | | 7/2001 | Braginsky et al. |
| 6,530,479 B2 | | 3/2003 | Hernandez |
| D568,494 S | | 5/2008 | Koseki |
| D569,525 S | | 5/2008 | Koseki |
| 7,441,655 B1 | * | 10/2008 | Hoftman ................ A61B 50/20 206/370 |
| 8,177,063 B1 | | 5/2012 | Simm et al. |
| 8,418,851 B2 | | 4/2013 | Culligan et al. |
| 9,706,989 B2 | | 7/2017 | Lee |
| 2010/0230300 A1 | | 9/2010 | Hunter et al. |
| 2016/0089139 A1 | | 3/2016 | Koman et al. |
| 2017/0079638 A1 | * | 3/2017 | Pereira ............... A61B 17/0485 |
| 2019/0099169 A1 | * | 4/2019 | Yoshimi ................ A61B 17/29 |
| 2019/0307446 A1 | * | 10/2019 | Chang ............... A61B 17/06066 |
| 2020/0405299 A1 | * | 12/2020 | Trauner ................ A61B 17/06 |

* cited by examiner

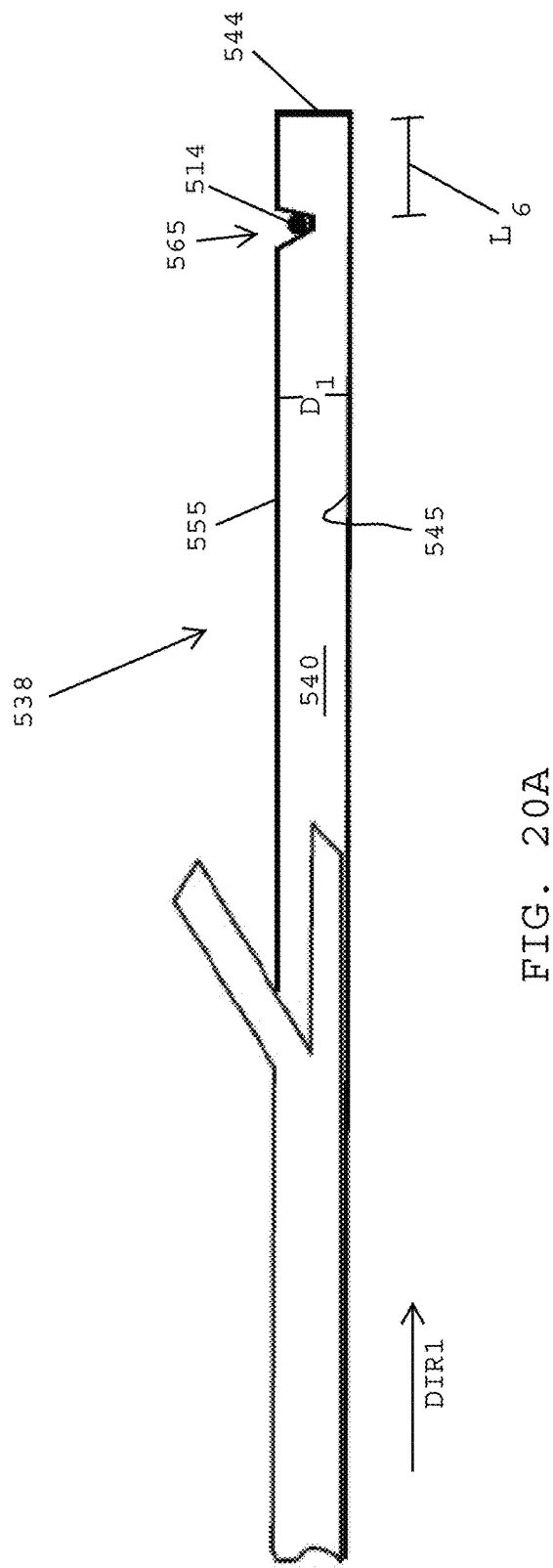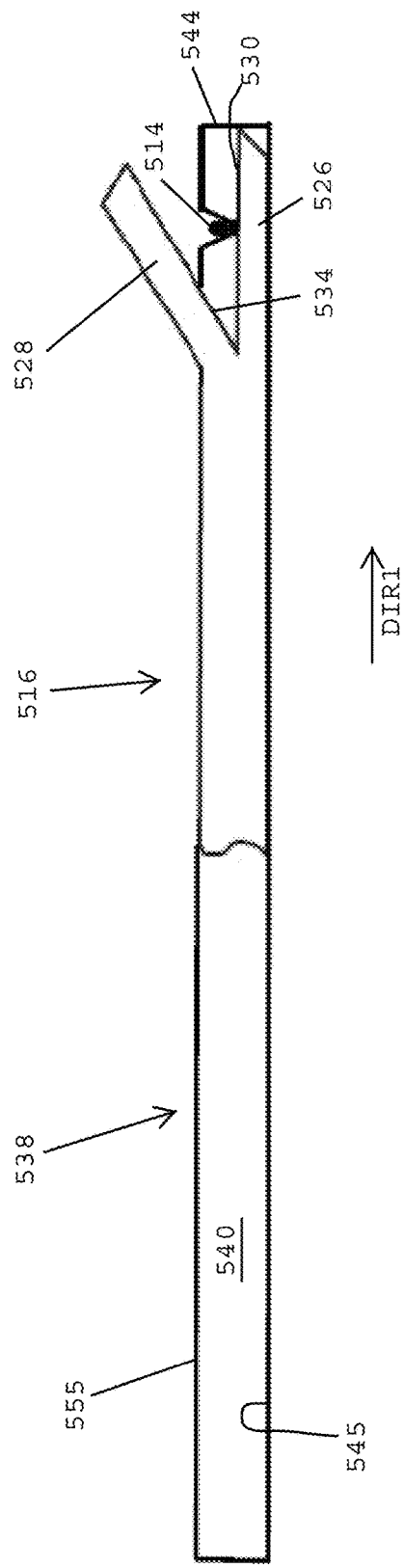
FIG. 20A
FIG. 20B

SUTURE NEEDLE PACKAGES FOR LOADING SUTURE NEEDLES AND METHODS OF PASSING SUTURE NEEDLES THROUGH TROCARS

BACKGROUND OF THE INVENTION

Field of the Invention

The present patent application is generally related to surgical procedures and surgical tools, and is more specifically related to systems, devices and methods for loading suture needles and passing suture needles through trocars.

Description of the Related Art

Surgeons use trocars to position surgical tools, such as suture needles, at surgical sites. The size of a suture needle (e.g., a needle attached to a suture) or a surgical needle (e.g., a needle not attached to a suture) that can be passed through the trocar to a surgical site is limited by the size of the opening in the trocar. In many instances, surgeons desire to use larger needles for closing surgical wounds and repairing anatomical features, however, passing larger needles through smaller trocars is difficult. For example, 5 mm trocars are often used during minimally invasive surgeries (MIS), however, surgeons cannot pass the larger suture needles through the 5 mm trocars so they are forced to use only smaller suture needles.

The smaller suture needles are less than optimal because, inter alia, they often require a surgeon to make many more passes of the needle and suture through tissue, which lengthens the surgical procedure and can frustrate the surgeon. Using smaller needles may also produce a bite distance that puts the wound or anatomical feature at risk of dehiscence.

In addition, larger-sized sutures cannot be easily attached to the smaller suture needles. Thus, when fine sutures are passed through tissue with a smaller bite size, a cheese wire effect may result, whereby the suture cuts through the tissue it is intended to hold.

Thus, there is a need for improved suture needles that can be passed through relatively smaller trocars (e.g., 5 mm trocars) for use in surgical procedures. There is also a need for systems, packages, devices and methods for passing larger suture needles through relatively smaller trocars.

SUMMARY OF THE INVENTION

As used herein, the terms surgical needle and suture needle are used interchangeably. A surgical needle may have a suture attached thereto or may not have a suture attached thereto. A suture needle may have a suture attached thereto or may not have a suture attached thereto. Regardless of whether the terms surgical needle or suture needle are used herein, the terms may be used to describe both needles having sutures attached thereto and needles that do not have sutures attached thereto.

In one embodiment, a surgical needle or suture needle is preferably made of a hyper-elastic and/or or superelastic material, such as Nitinol. In one embodiment, the suture needle may be elastically deformed to lower the height and/or the profile of the suture needle to pass the suture needle through a trocar, such as a trocar having a diameter of 5 mm or smaller.

In one embodiment, a needle driver may be used to secure a tapered section at a distal end of the suture needle with the barrel of the suture needle trailing behind the tip of the suture needle. In one embodiment, the tip is preferably surrounded by clamping jaws at the distal end of the needle driver for protecting the tip as the suture needle is passed through a trocar. The clamping jaws preferably surround and protect the tip for preventing the tip from contacting the inside of the trocar as it is passed through the trocar, which could damage the tip during its passage through the channel of the trocar.

In one embodiment, when the suture needle is held by the needle driver, the tip of the needle does not extend or protrude outside the external surface of the needle holder.

In one embodiment, a suture needle package preferably includes a base, and a needle driver alignment guide overlying the base, the needle driver alignment guide including first and second lateral guide walls that oppose one another for defining a needle driver guide channel.

In one embodiment, a suture needle desirably overlies the base. The suture needle may include a proximal end and a distal end having a tapered section that terminates at a tip. In one embodiment, at least one connector releasably secures the suture needle over the base. In one embodiment, the at least one connector desirably orients the suture needle relative to the first and second lateral guide walls so that the tip of the suture needle is located within the suture needle guide channel and is bounded by the first and second lateral guide walls.

In one embodiment, the needle driver guide channel preferably has a proximal end, a distal end, and a longitudinal axis that extends between the proximal and distal ends thereof.

In one embodiment, the needle driver alignment guide may include an end wall interconnecting the first and second lateral guide walls for defining the distal end of the needle driver guide channel. In one embodiment, the end wall desirably interconnects distal ends of the first and second lateral guide walls. In one embodiment, the first and second lateral guide walls are desirably parallel to one another.

In one embodiment, the end wall and the distal ends of the first and second lateral side walls preferably surround the tip of the suture needle.

In one embodiment, each of the first and second lateral guide walls has a lower end and an upper free end, and the at least one connector holds the tip of the suture needle between the lower ends and the upper free ends of the respective first and second lateral guide walls.

In one embodiment, the at least one connector preferably secures the tip of the suture needle closer to the distal end of the needle driver guide channel and secures the proximal end of the suture needle closer to the proximal end of the needle driver guide channel.

In one embodiment, the at least one connector may include a securing notch formed in the upper free end of one of the first and second lateral guide walls. In one embodiment, the tapered section of the suture needle is seated in the securing notch and the tapered section extends proximally from the tip of the suture needle.

In one embodiment, the tapered section of the suture needle preferably extends along an axis that defines an angle with the longitudinal axis of the needle driver alignment channel of less than 90 degrees, which preferably enables the suture needle to be passed through a trocar using less force.

In one embodiment, the at least one connector may include a second connector that is located proximal to the securing notch for securing a section of the suture needle that is proximal to the tapered section of the suture needle.

In one embodiment, the suture needle may be made of an elastic, hyper-elastic, or superelastic material or alloy such as Nitinol.

In one embodiment, a system for aligning a needle driver with a tip of a suture needle may include a suture needle package having a base, a needle driver alignment guide overlying the base, and at least one connector for releasably securing the suture needle to the suture needle package.

In one embodiment, the needle driver alignment guide preferably includes first and second lateral guide walls that oppose one another for defining a needle driver guide channel. In one embodiment, an end wall desirably interconnects the first and second lateral guide walls for defining a distal end of the needle driver alignment guide.

In one embodiment, a suture needle desirably overlies the base. The suture needle may include a proximal end and a distal end having a tapered section that terminates at a tip.

In one embodiment, the at least one connector preferably secures the suture needle over the base and controls the orientation of the suture needle so that the tip of the suture needle is located within the suture needle guide channel and is bounded by the end wall and the first and second lateral guide walls.

In one embodiment, a needle driver may have an elongated shaft and a clamping assembly located at a distal end of the elongated shaft. In one embodiment, the clamping assembly engages the end wall of the needle driver alignment guide for aligning the clamping assembly with the tip of the suture needle.

In one embodiment, the at least one connector desirably holds the tip of the suture needle between the first and second lateral guide walls so that the tip is spaced away from the first and second lateral guide walls.

In one embodiment, the at least one connector may hold the tip of the suture needle proximal to and spaced away from the end wall of the needle driver alignment guide by a first distance.

In one embodiment, a clamping assembly preferably has a lower jaw with a top surface and an opposing upper jaw with a bottom surface that is pivotally coupled with the lower jaw for moving the clamping assembly between open and closed positions. In one embodiment, a distal end of the lower jaw engages the end wall, whereupon the top surface of the lower jaw is aligned with the tip of the suture needle.

In one embodiment, the top surface of the lower jaw preferably has a length that extends between a proximal end and the distal end thereof. In one embodiment, the length of the top surface of the lower jaw is desirably greater than the first distance between the tip of the suture needle, secured by a connector, and the end wall of the needle driver alignment guide.

In one embodiment, when the clamping assembly is abutted against the end wall of the alignment guide, the upper jaw of the clamping assembly is desirably positioned over the tip of the suture needle and the lower jaw of the clamping assembly is desirably positioned under the tip of the suture needle.

In one embodiment, the first and second lateral guide walls are spaced from one another to define a width of the needle driver alignment guide.

In one embodiment, a resilient element, such as a foam pad or one or more springs, may be disposed between the first and second lateral guide walls for urging a needle driver against one of the first and second lateral guide walls.

In one embodiment, the elongated shaft of the needle driver has a width that is substantially equal to the width of the needle driver alignment guide.

In one embodiment, the elongated shaft of the needle driver has an outer diameter, and the needle driver alignment guide preferably has a depth that is about % the dimension of the outer diameter of the elongated shaft of the needle driver.

In one embodiment, a method of delivering a suture needle to a surgical site desirably includes obtaining a suture needle package having a needle driver alignment channel, and a suture needle secured to the suture needle package, the suture needle having a distal end with a tapered section that terminates at a tip, whereby the tapered section and the tip of the suture needle are positioned within the needle driver alignment channel.

In one embodiment, a method includes positioning a needle driver in the needle driver alignment channel, the needle driver having a clamping assembly at a distal end thereof that is moveable between open and closed positions.

In one embodiment, with the clamping assembly of the needle driver in the open position, the clamping assembly is preferably advanced along a longitudinal axis of the needle driver alignment channel toward a distal end of the needle driver alignment channel for aligning the clamping assembly with the tip of the suture needle.

In one embodiment, after the clamping assembly reaches the end of the needle driver alignment channel (e.g., tactile feedback of abutting against the end wall), the clamping assembly may be moved to the closed position for clamping the portion of the tapered section of the suture needle that is positioned within the needle driver alignment channel. In one embodiment, the closed clamping assembly preferably covers the tip for preventing exposure of the tip outside the clamping assembly.

In one embodiment, the closed clamping assembly may be used for lifting the suture needle out of the suture needle package.

In one embodiment, with the proximal end of the suture needle trailing the tip of the suture needle, the closed clamping assembly may be used for passing the suture needle through a trocar.

In one embodiment, the suture needle is made of an elastic material such as a hyper-elastic material or a superelastic material (e.g., Nitinol).

In one embodiment, the suture needle preferably has a more curved configuration (e.g., a half-circle shape or higher profile) when secured to the suture needle package and a less curved configuration (e.g. a flatter shape or lower profile) during passing the suture needle through the trocar.

In one embodiment, the suture needle may be loaded onto the needle driver using one hand.

In one embodiment, a system may include a suture needle package and a needle driver packaged together, whereby the needle driver is used for removing one or more suture needles or surgical needles from the package.

In one embodiment, the suture needle is preferably releasably secured to the suture needle package, such as by using one or more friction fit or snap-fit connectors that engage the outer surface of the suture needle.

In one embodiment, the needle driver may have elongated shafts having different outer diameters or widths of about 3-8 mm and more preferably about 5 mm.

In one embodiment, the suture needle package, the suture needle, and the needle driver are preferably sterilizable, biocompatible, and stable.

In one embodiment, a suture needle package preferably includes a needle driver guide channel that is configured to guide a needle driver into alignment with a distal tip of a suture needle that is releasably secured to the package.

In one embodiment, the suture needle package preferably includes one or more connectors that releasably secure a suture needle to the package, wherein the one or more connectors form a snap-fit, a friction fit, and/or a releasable connection with the suture needle so that the suture needle may be easily released from the package when secured by the needle driver.

In one embodiment, at least one of the connectors preferably orients the suture needle at a preferred angle relative to the needle driver and the needle driver guide channel.

In one embodiment, a resilient element or spring may be disposed within the needle driver guide channel for urging an elongated shaft of a needle driver against an opposite guide wall of the needle driver guide channel. In one embodiment, if the needle driver guide channel has a width that is greater than the width or outer diameter of the elongated shaft of the needle driver, the resilient element or spring takes up the slack or space to engage the elongated shaft, which makes sure that different sized needle holders will align with the tip of the suture needle with the tip not protruding outside the clamping jaws of the needle driver.

In one embodiment, the needle driver guide channel may include a hard stop or a tactile indicator that aids a surgeon to align the clamping assembly with the tip of the suture needle.

In one embodiment, the needle driver alignment guide has a low profile so that is may be integrated into existing suture needle package designs.

In one embodiment, the needle driver alignment guide may have an open window on top to access the needle tip in the suture needle package. In one embodiment, the needle driver alignment guide may have an opening on the side for accessing the tipoff the suture needle.

The needle driver alignment guide preferably enables a needle holder to be consistently aligned with the tip of the suture needle, for clamping onto a tapered section of the needle that is proximal to the tip, without exposing the tip to possible damage during transfer through a trocar.

In one embodiment, the angle of the needle relative to the long axis of the needle driver may be controlled to minimize the amount of force that is required to advance (e.g., push, pull) the suture needle force through a trocar.

In one embodiment, after the needle driver is closed, the suture needle may be lifted from the suture package for direct introduction through the trocar.

In one embodiment, direct loading of the suture needle from the suture package prevents accidental stabbing of surgical personnel.

In one embodiment, obtaining access to the suture needle may be possible through either the top or the side of the suture needle package.

In one embodiment, the needle driver guide channel may be made of paper, which may also be used to control moisture levels within a suture needle package.

In one embodiment, the needle driver alignment guide is visible to a surgeon (e.g., visible on a top side of a suture needle package) to provide a simple, intuitive design for securing the tip of a suture needle with a needle driver or clamping element.

In one embodiment, a needle driver alignment guide may be readily incorporated into an existing design for a suture needle package without requiring modification of the existing design.

In one embodiment, the needle driver guide channel preferably controls the direction and the angle of the needle holder relative to the tip and the tapered section of the suture needle when loading the suture needle.

In one embodiment, the inside geometry of the needle driver guide channel desirably matches the geometry of the needle holder.

In one embodiment, the needle driver alignment guide preferably stops the introduction of the needle holder when the tip of the needle is aligned with the jaws of the clamping assembly.

These and other preferred embodiments of the present invention will be described in more detail below.

BRIEF DESCRIPTION OF THE DRAWINGS

FIG. 5A-1 shows the suture needle and the needle driver of FIG. 5A with the upper jaw of the clamping assembly removed.

FIG. 20A shows a first stage of a method of aligning a distal end of a needle driver with a tip of a suture needle, in accordance with one embodiment of the present patent application.

FIG. 20B shows a second stage of a method of aligning a distal end of a needle driver with a tip of a suture needle, in accordance with one embodiment of the present patent application.

DETAILED DESCRIPTION OF PREFERRED EMBODIMENTS

Figure 1A:
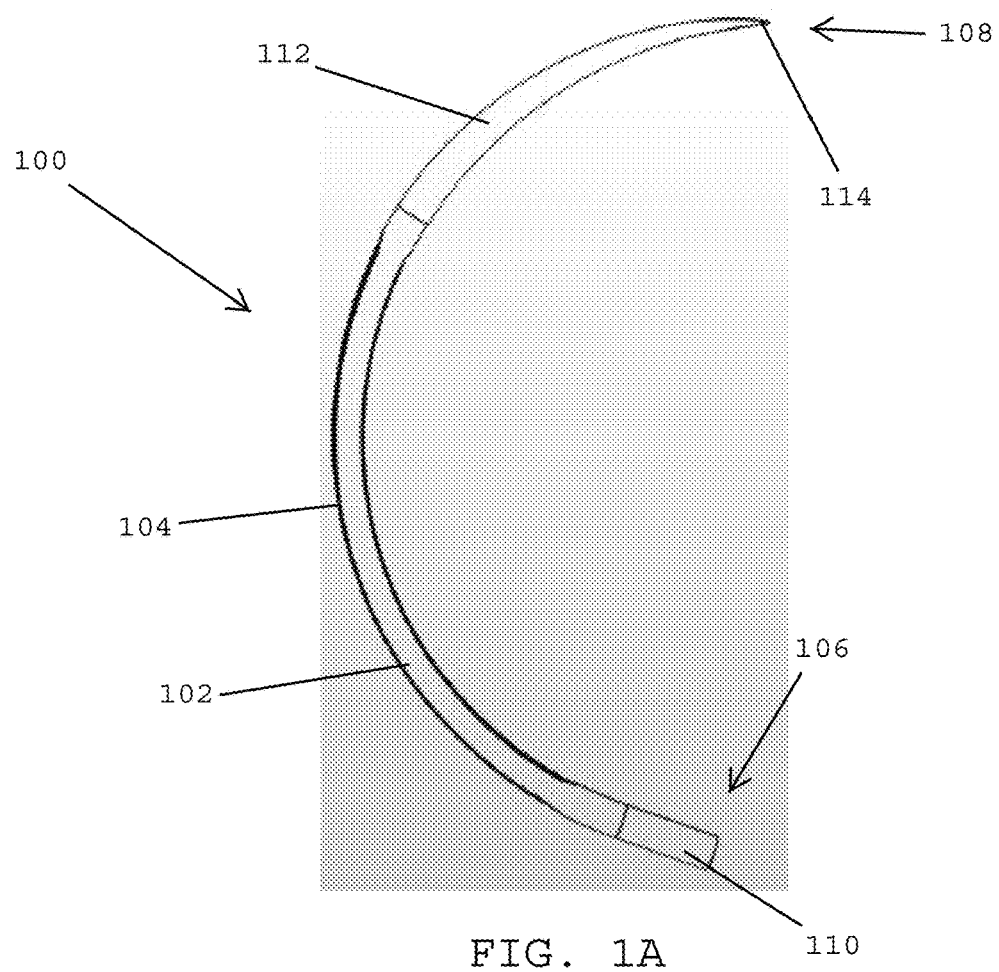
FIG. 1A is a side view of a suture needle having a proximal end and a distal end with a tapered section and a distal tip, in accordance with one embodiment of the present patent application.
Figure 1B:
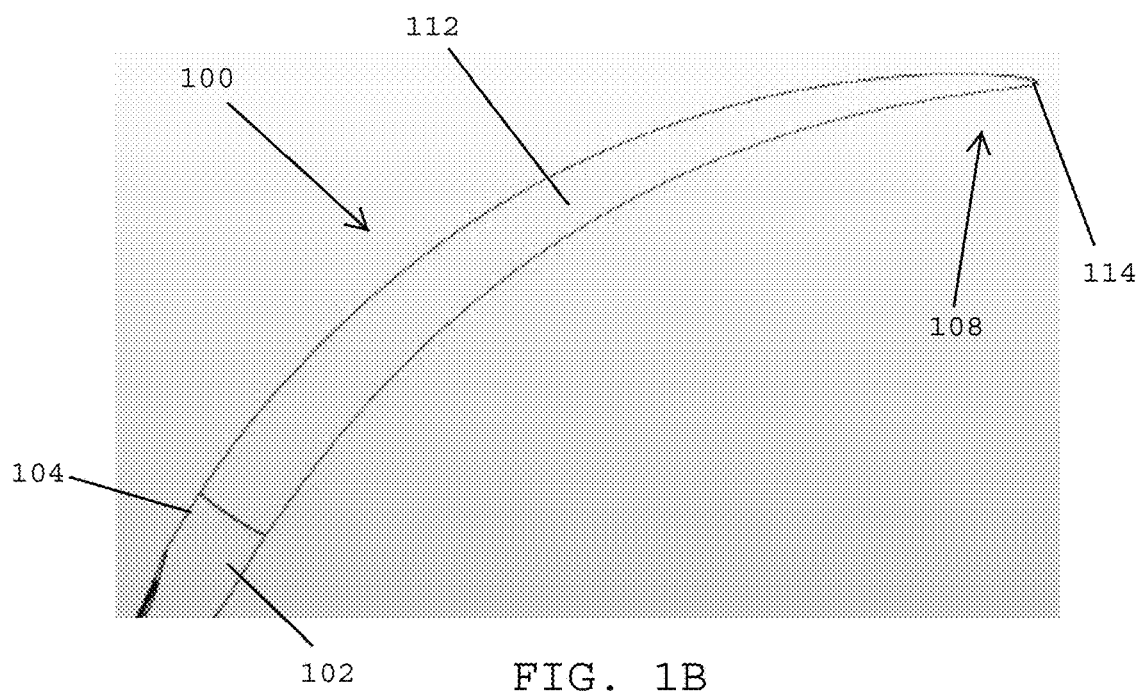
FIG. 1B is a magnified view of the tapered section and the distal tip of the suture needle shown in FIG. 1A.

Referring to FIGS. 1A and 1B, in one embodiment, a suture needle 100 preferably includes an elongated body 102 having an outer surface 104 that extends from a proximal end 106 to a distal end 108 of the suture needle. In one embodiment, the suture needle 100 is preferably made of an elastic, hyper-elastic, or superelastic material, such as Nitinol, whereby an external force may be applied to the suture needle to elastically deform the suture needle, and the suture needle will spring back to its original shape and/or configuration when the external force is removed. In one embodiment, the elongated body 102 of the suture needle 100 is curved and may have a semi-circular or circular shaped segment. In one embodiment, the suture needle defines a half circle or semi-circle. In one embodiment, the suture needle defines ¼ of a circle, ⅜ of a circle, ⅝ of a circle, ¾ of a circle, etc.

In one embodiment, the suture needle 100 preferably includes a suture attachment barrel 110 that is located at the proximal end 106 of the elongated body 102, which preferably has a suture attachment opening formed in a proximal face thereof. In one embodiment, a distal end of a surgical suture may be inserted into the suture attachment opening of the suture attachment barrel 110 and the barrel may be swaged for securing the surgical suture to the proximal end 106 of the suture needle 100.

In one embodiment, the distal end 108 of the suture needle 100 preferably includes a tapered section 112 that tapers inwardly to a tip 114 that is located at a distal-most end of the suture needle. The tip 114 may be sharpened for piercing tissue to facilitate passing the suture needle through tissue during a suturing operation.

In one embodiment, the suture needle may have a bendable region or may be highly elastic for changing shape and/or configuration to fit through a trocar (e.g., a 5 mm trocar), as disclosed in commonly assigned U.S. patent application Ser. No. 16/282,604, filed Feb. 22, 2019, published as U.S. Ser. No. 2020/0268378, Ser. No. 16/282,652, filed on Feb. 22, 2019, published as U.S. Ser. No. 2020/0268379, and Ser. No. 16/781,055, filed Feb. 4, 2020, which claims benefit of U.S. Provisional Application Number 62/809,016, filed on Feb. 22, 2019, and now published as U.S. 2020/0268380, the disclosures of which are hereby incorporated by reference herein.

Figure 2A:
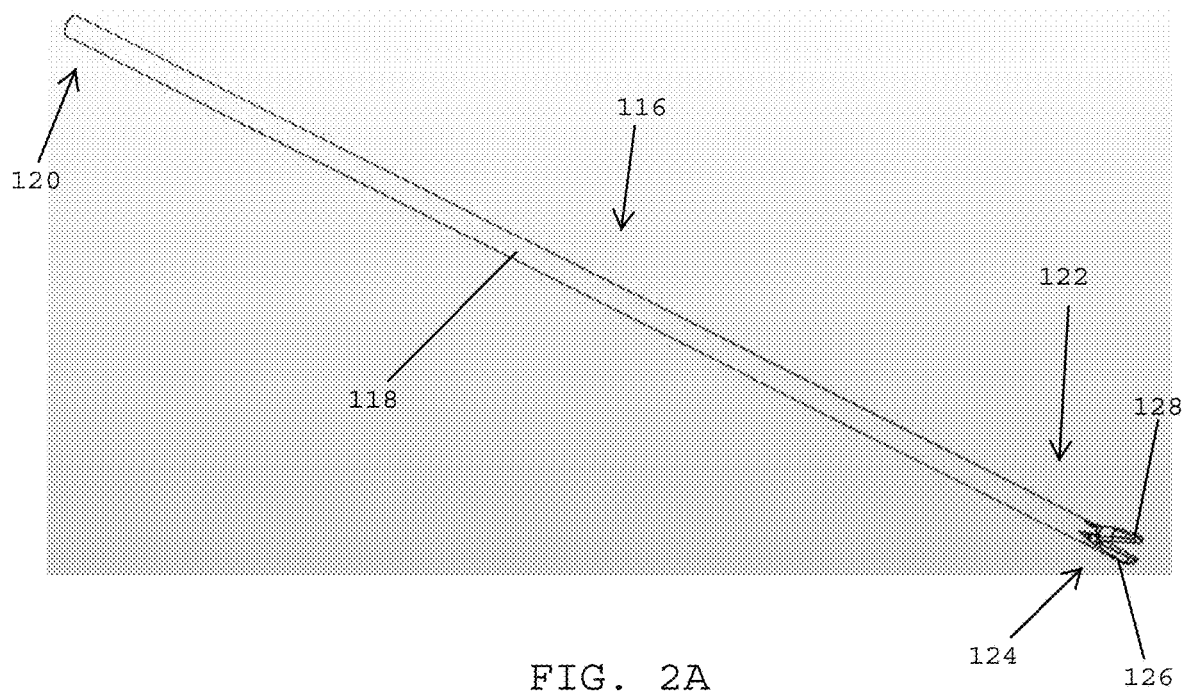
FIG. 2A is a perspective view of a needle driver having an elongated shaft with a proximal end, a distal end, and a clamping assembly at the distal end of the elongated shaft, the clamping assembly including lower and upper jaws moveable between open and closed positions, in accordance with one embodiment of the present patent application.
Figure 2B:
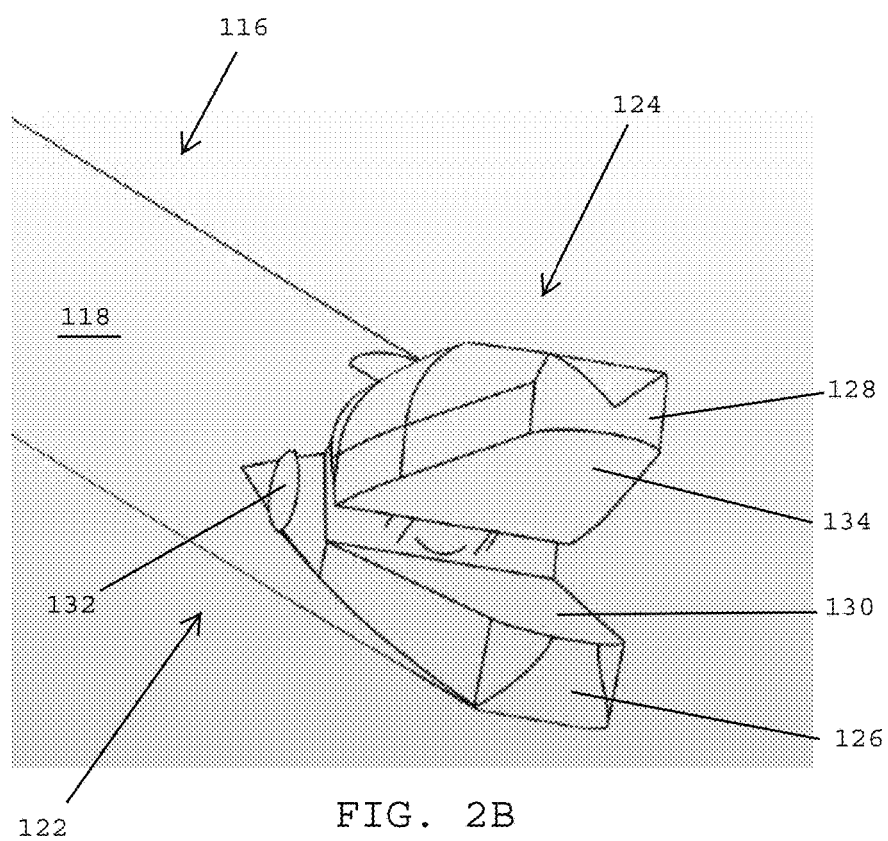
FIG. 2B is a perspective view of the distal end of the elongated shaft and the clamping assembly of the needle driver shown in FIG. 2A.

Referring to FIGS. 2A and 2B, in one embodiment, a clamping element such as a needle driver 116 may be utilized for securing a suture needle, such as the suture needle 100 shown in FIGS. 1A and 1B, to remove the suture needle from a suture needle package and advance the clamped suture needle through a trocar to a surgical site for performing a suturing operation. In one embodiment, the shape of the suture needle may change as the needle driver 116 advances the suture needle through the trocar. For example, the suture needle may be a superelastic suture needle that normally has a semi-circular shape with a first height. As the needle driver advances the suture needle through the trocar having a smaller inner diameter than the first height of the suture needle, the suture needle will flatten out or become straighter along at least one segment for assuming a smaller, second height for fitting through the smaller trocar. Upon being extracted from the end of the trocar, the superelastic suture needle will preferably return (e.g., spring back) to its original first height and the original semi-circular shape.

In one embodiment, the needle driver 116 preferably includes an elongated shaft 118 having a proximal end 120 and a distal end 122 including a clamping assembly 124 that is movable between open and closed positions. In one embodiment, the clamping assembly 124 preferably includes a lower jaw 126 and an opposing upper jaw 128 that is movable between open and closed positions. In one embodiment, with the clamping assembly 124 in the open position, the lower and upper jaws 126, 128 may be guided into alignment with a tip of a suture needle. In one embodiment, after the lower and upper jaws are aligned with the tip of the suture needle, the jaws may be moved to the closed position for clamping and/or gripping the tapered section of the suture needle with the tip positioned between and surrounded by the opposing lower and upper jaws.

Referring to FIG. 2B, in one embodiment, the lower jaw 126 may be stationary and/or rigidly secured to the distal end 122 of the elongated shaft 118 of the needle driver 116 so that the lower jaw 126 is fixed and does not move relative to the distal end 122 of the elongated shaft 118 of the needle driver 116. In one embodiment, the lower jaw 126 preferably includes a substantially flat top surface 130 that is adapted to be aligned with the tip 114 (FIG. 1B) that is located at the distal end of the suture needle. In one embodiment, the substantially flat top surface 130 of the lower jaw 126 may include a surface roughening such as knurling for enhancing gripping of the tapered section 112 (FIG. 1B) of the suture needle when the clamping assembly 124 is in the closed position.

In one embodiment, the upper jaw 128 of the clamping assembly 124 is desirably pivotally secured to the distal end 122 of the elongated shaft 118 of the needle driver 116 via a pivot 132, which pivotally secures a proximal end of the upper jaw 128 to the distal end 122 of the elongated shaft 118. The upper jaw 128 preferably includes a substantially flat bottom surface 132 that opposes the substantially flat top surface 130 of the lower jaw 126. The substantially flat bottom surface 134 of the upper jaw 128 may include surface roughening such as knurling for gripping the tapered section 112 (FIG. 1B) of a suture needle when the clamping assembly 124 is in the closed position.

In one embodiment, when the lower and upper jaws 126, 128 are in the closed position for clamping, gripping and/or securing the distal end of the suture needle, the top surface 130 of the lower jaw 126 and the bottom surface 134 of the upper jaw 128 preferably engage the tapered section of the suture needle that is located between the jaws, however, the top and bottom surfaces of the jaws are spaced away from the tip so that the tip is not marred or dulled by the jaws of the clamping assembly.

Figure 3:
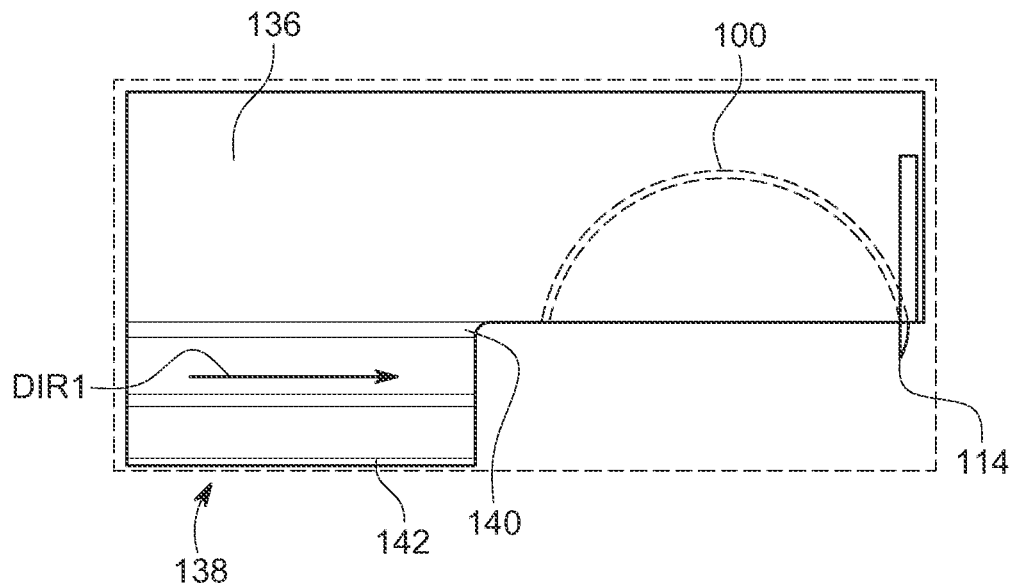
FIG. 3 shows a suture needle package for a suture needle including a needle driver alignment guide, in accordance with one embodiment of the present patent application.
Figure 4:
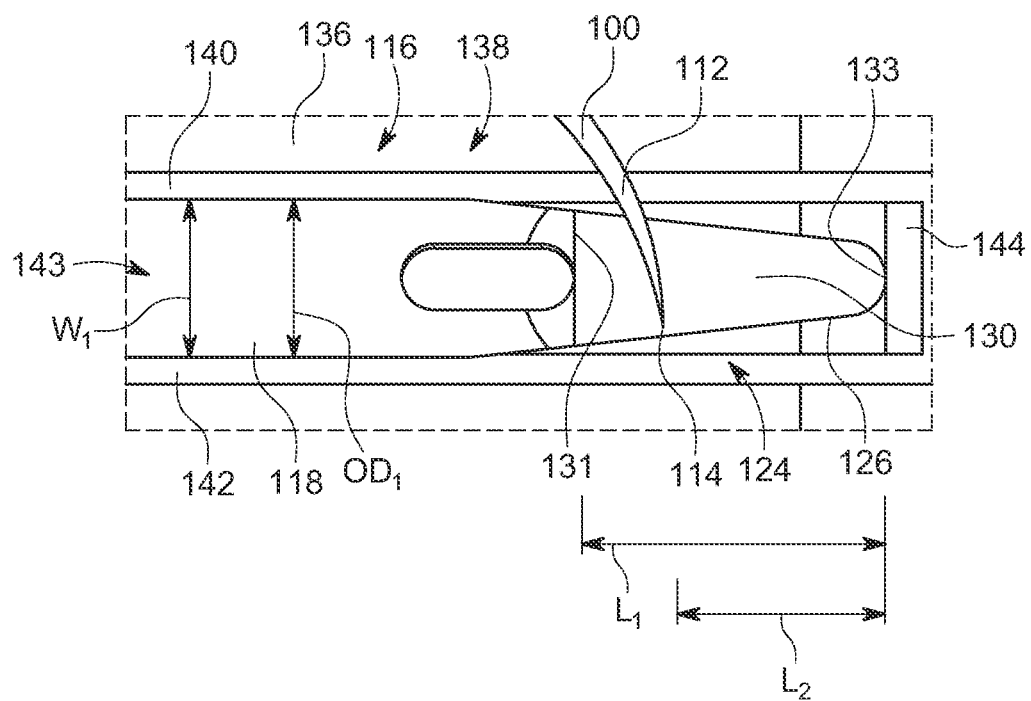
FIG. 4 is a top plan view of a suture needle package having a needle driver alignment guide that guides a distal end of the needle driver into alignment with a tip of a suture needle, in accordance with one embodiment of the present patent application.

Referring to FIGS. 3 and 4, in one embodiment, a suture needle package 136 preferably holds a suture needle 100, such as the suture needle shown in FIGS. 1A and 1B, so that the tip 114 of the suture needle 100 is pre-positioned at a location that will facilitate aligning the tip 114 of the suture needle 100 between the top and bottom surfaces 130, 134 of the respective upper and lower jaws 126, 128 of the clamping assembly 124 of the needle driver 116.

In one embodiment, the suture needle package 136 preferably includes a needle driver alignment guide 138 having a first lateral guide wall 140 and an opposing second lateral guide wall 142 that preferably engage the lateral sides of the elongated shaft 118 of the needle driver 116 (FIG. 2A) for guiding the clamping assembly of the needle driver in the direction designated DIR1 for aligning the lower and upper jaws of the clamping assembly 124 with the tip 114 of the suture needle 100 to ensure that the tip 114 is positioned between the top and bottom surfaces of the respective upper and lower jaws of the clamping assembly. In one embodiment, the first and second lateral guide walls 140, 142 define a needle driver guide channel 143, which preferably aligns the needle driver with the tip 114 as the needle driver moves in the direction DIR1 toward the tip 114.

Referring to FIG. 4, in one embodiment, the suture needle package 136 preferably includes one or more releasable connectors that releasably secure the suture needle to the suture needle package. In one embodiment, the one or more releasable connectors desirably hold the tip 114 of the suture needle 100 at a known location having three dimensions, between the first lateral guide wall 140 and the opposing second lateral guide wall 142 so that jaws of the clamping assembly 124 may be consistently aligned with the tip 114 as the needle driver 116 is advanced in the direction designated DIR1 through the needle driver guide channel 143 defined by the needle driver alignment guide 138. In one embodiment, the needle driver 116 preferably includes the elongated shaft 116 having an outer diameter $OD_1$ that closely matches the width $W_1$ of the needle driver alignment guide 138, which is preferably defined as the distance between the first lateral guide wall 140 and the opposing second lateral guide wall 142. In one embodiment, if the outer diameter of the elongated shaft of the needle driver is less than the width of the needle driver alignment guide, a resilient element (e.g., a foam strip, a spring) may be inserted into the needle driver alignment guide for engaging the side of the elongated shaft for urging the shaft against one of the first and second lateral guide walls. The needle driver alignment guide preferably has a depth that is about equal to ½ the diameter of the elongated shaft 118 of the needle driver 116 so that the space between the opposing lower and upper jaws is aligned with the tip 114 of the suture needle.

In one embodiment, as the elongated shaft 118 of the needle driver 116 is advanced through the needle driver alignment guide 138 in a direction designated DIR1, the clamping assembly 124 will preferably advance distally until a distal-most end of the lower jaw 126 abuts against a hard stop 144 that is located at a distal end of the needle driver alignment guide 138. In one embodiment, when the distal-most end of the lower jaw 126 abuts against the hard stop 144, the flat top surface 130 of the lower jaw 126 is preferably aligned with the tip 114 of the suture needle 100. With the suture needle package holding the tip of the suture needle at a known location having X, Y and Z coordinates, the needle driver alignment guide preferably controls the position of the lower and upper jaws along respective X, Y and Z axes to ensure that the tip is consistently and repeatedly positioned between the opposing clamping faces of the lower and upper jaws. In one embodiment, the top surface 130 of the lower clamping jaw 126 has a length $L_1$ that is greater than the distance $L_2$ between the tip 114 and the proximal face of the hard stop 144, which ensures that the tip 114 will be located between the proximal and distal ends 131, 133 of the top surface 130 of the lower jaw 126. As a result, the tip 114 will generally be aligned midway between the proximal and distal ends 131, 133 of the top surface 130 of the lower jaw 126. In one embodiment, similar dimensions are provided for the bottom surface of the upper jaw to insure that the tip is positioned approximately midway between the proximal and distal ends of the upper jaw of the clamping assembly.

As will be described in more detail herein, the upper jaw of the clamping assembly 124 (FIG. 2B) may be moved to the closed position for engaging the tapered section 112 of the suture needle 100 to secure the tip 114 of the suture needle 100 between the lower and upper jaws of the needle driver 116. In one embodiment, the clamping faces of the lower and upper jaws do not contact the tip, but rather clamp onto the thicker, tapered section of the suture needle to avoid damaging or dulling the tip.

Figure 5A:
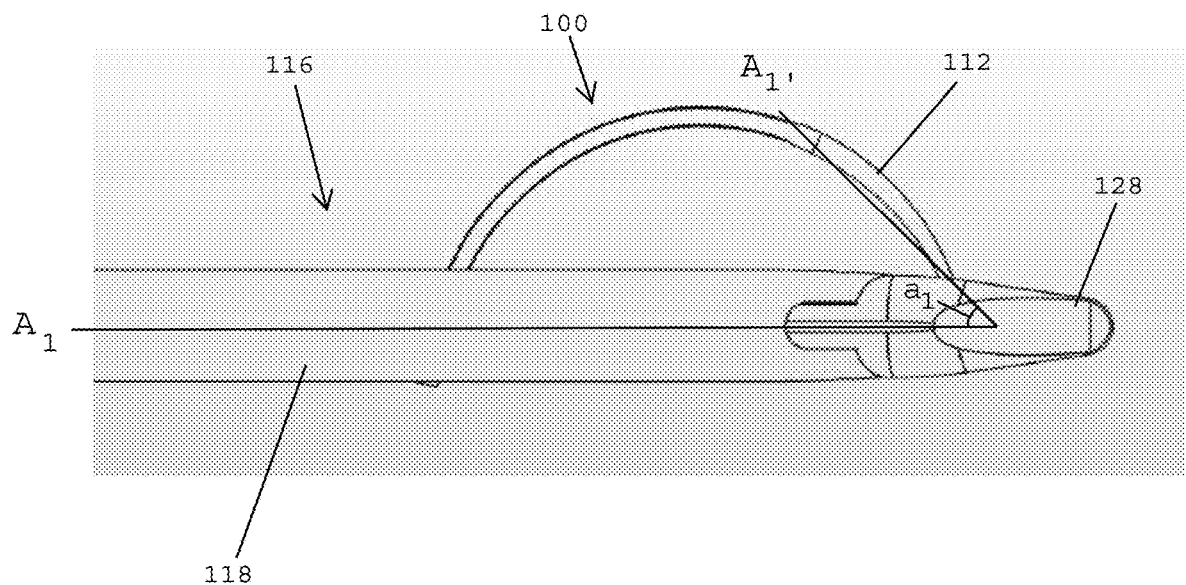
FIG. 5A shows a tip of a suture needle aligned with the lower and upper jaws of the clamping assembly of the needle driver of FIGS. 2A and 2B, in accordance with one embodiment of the present patent application.
Figures 1, 5A:
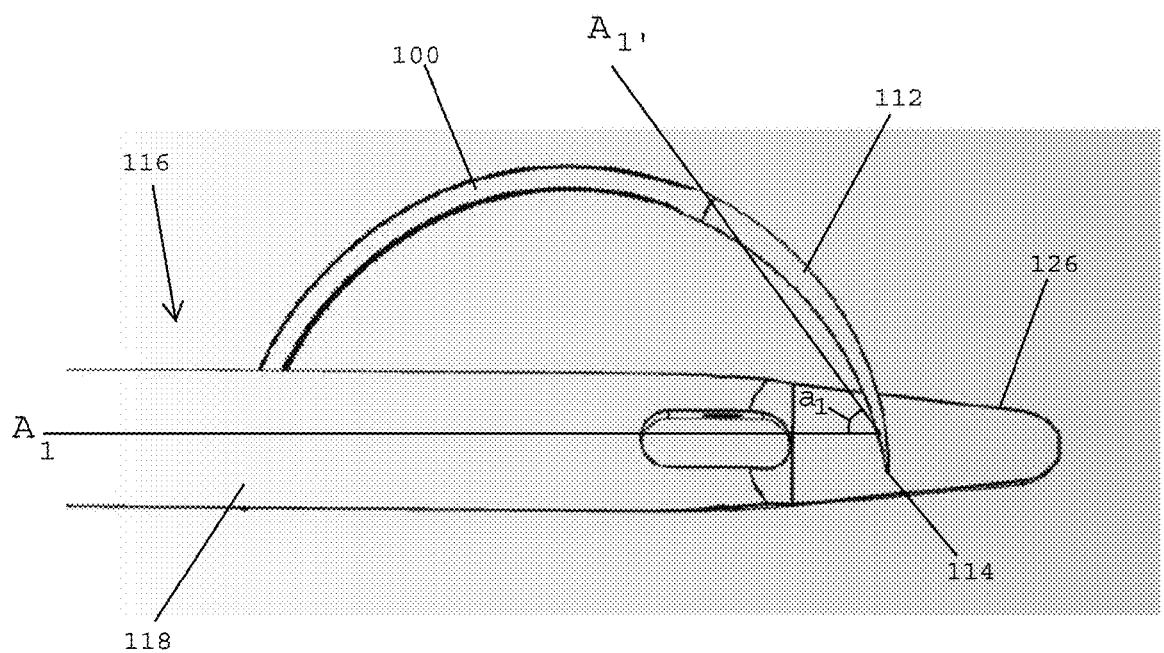

Referring to FIGS. 5A and 5A-1, in one embodiment, the needle driver 116 preferably includes the elongated shaft 118 having a longitudinal axis $A_l$ that extends between the proximal and distal ends of the elongated shaft 118. In one embodiment, as a result of the suture needle being held on the suture needle package in a pre-determined orientation, when the tip 114 of the suture needle 100 is secured between the lower and upper jaws 128, 126 of the clamping assembly, the tapered section 112 of the suture needle 100 preferably extends along an axis $A_1$ that defines an angle $\alpha_1$ that is less than 90 degrees relative to the longitudinal axis $A_1$ of the elongated shaft 118 of the needle driver 116. Holding the suture needle 100 at an angle that is less than 90 degrees preferably minimizes the amount of force that is required when using the needle driver to push or pull the suture needle though a trocar.

Figure 5B:
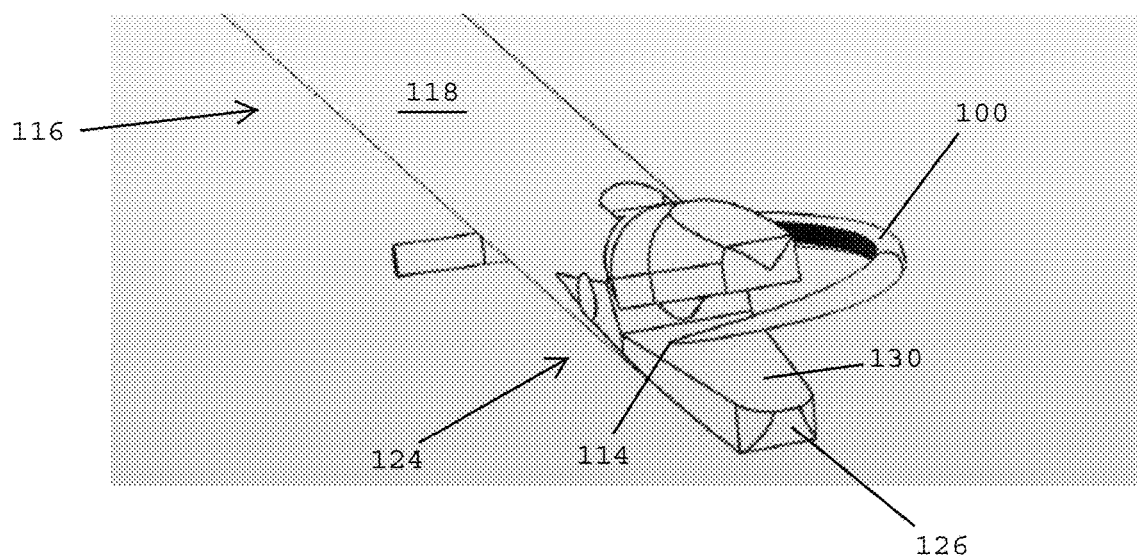
FIG. 5B shows a perspective end view of the needle driver of FIG. 5A.
Figure 5C:
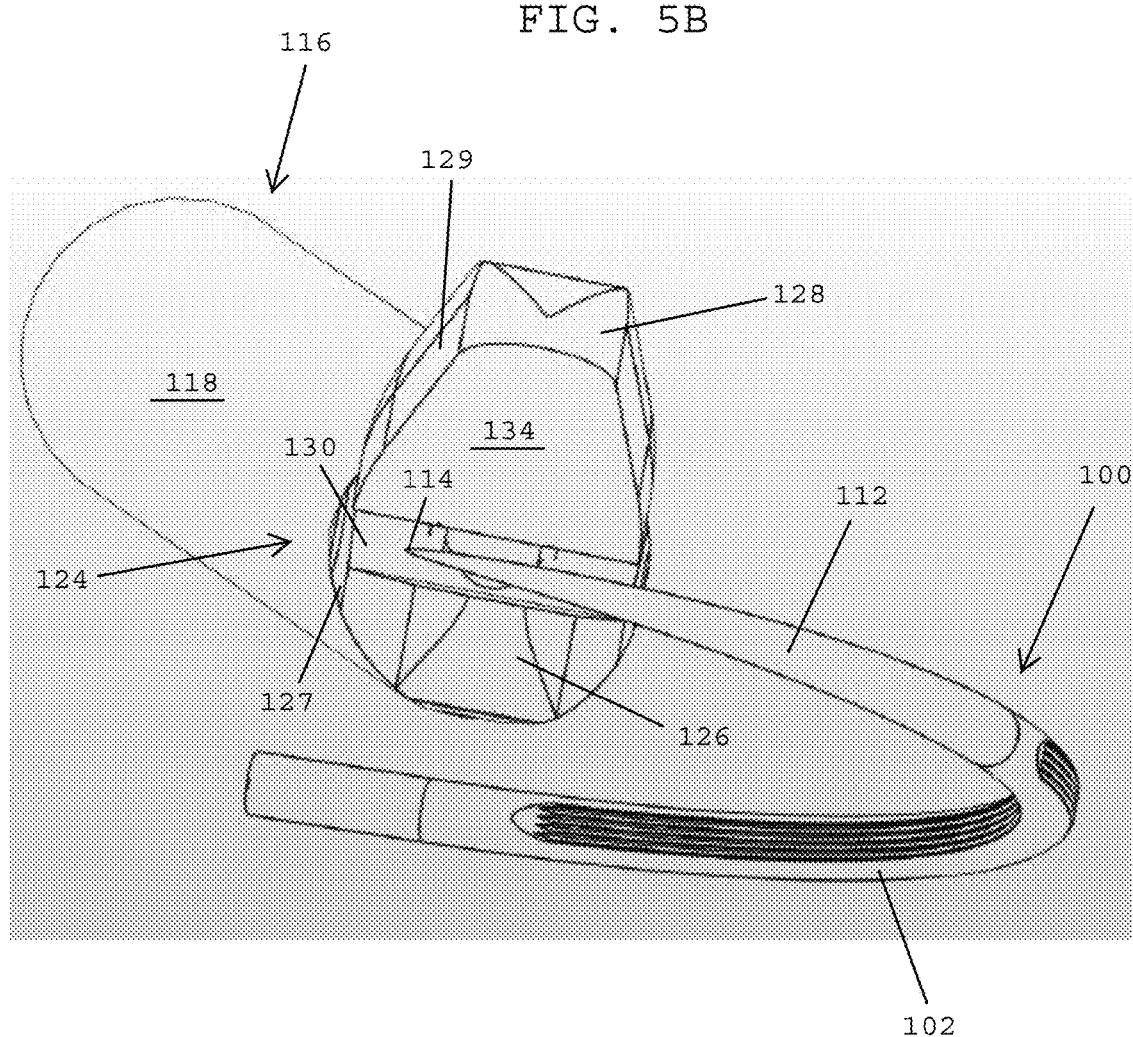
FIG. 5C shows another perspective end view of the needle driver shown in FIG. 5A.

Referring to FIGS. 5B and 5C, in one embodiment, the needle driver alignment guide 138 (FIGS. 3 and 4) preferably aligns the clamping assembly 124 of the needle driver 116 with the tip 114 of the suture needle 100 along the X, Y, and Z axes. In one embodiment, after using the needle driver alignment guide for aligning the clamping assembly with the suture needle, the tip 114 is preferably disposed between the top surface 130 of the lower jaw 126 and the bottom surface 134 of the upper jaw 128 of the clamping assembly 124. The elongated body 102 of the suture needle 100 preferably extends proximally toward the proximal end of the elongated shaft 118 of the needle driver 116.

In one embodiment, the engagement of the needle driver with the needle driver alignment guide insures that the tip 114 of the suture needle 100 is preferably aligned between the top and bottom surfaces 130, 134 of the respective lower and upper jaws 126, 128 so that the tip 114 is not exposed and/or does not extend beyond or outside the lateral sides 127, 129 of the respective lower and upper jaws 126, 128. Aligning the tip 114 of the suture needle 100 between the lower and upper jaws so that the tip 114 it is not exposed outside the jaws of the clamping assembly 124 will desirably protect the tip 114 as the needle driver 116 advances the suture needle 100 through a trocar. As a result, the protected tip will not be exposed and will not scratch the inside of the trocar, which could weaken, dull and/or damage the tip.

Referring to FIG. 5C, in one embodiment, the tapered section 112 of the suture needle 100 tapers inwardly toward the tip 114 that is located at the distal end of the suture needle 100. As a result, the tapered section 112 of the suture needle becomes thinner toward the tip 114. In one embodiment, when the clamping assembly 124 is closed, the opposing top and bottom surfaces of the respective lower and upper jaws 126, 128 engage a thicker portion of the tapered section 112 of the suture needle so that the tip 114 is not engaged by the opposing faces of the lower and upper jaws. Thus, in one embodiment, the clamping jaws provide a protective shroud or barrier around the tip of the suture needle, however, the clamping surfaces of the lower and upper jaws do not directly contact or engage the tip of the suture needle.

Figure 6:
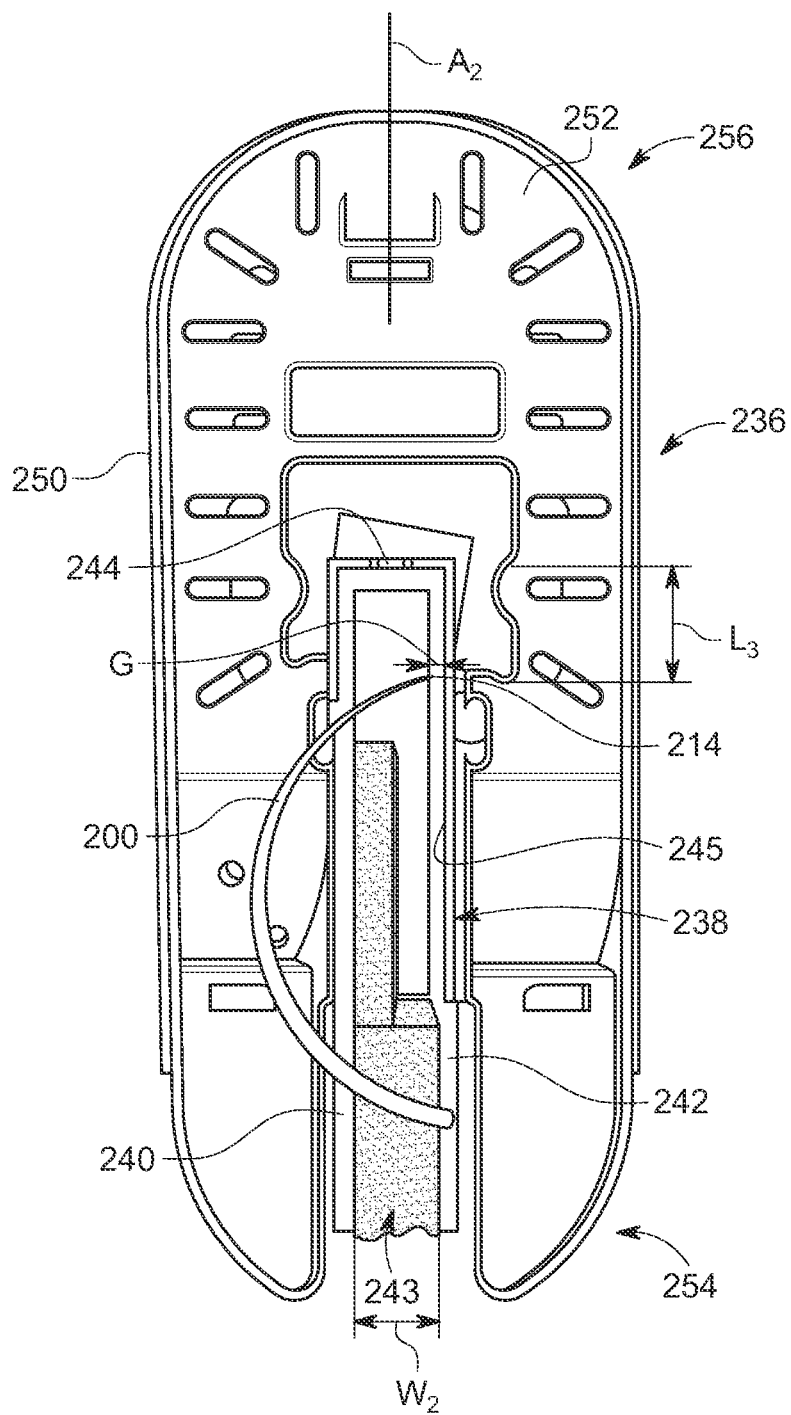
FIG. 6 is a top plan view of a suture needle package for a suture needle, the suture needle package having a needle driver alignment guide, in accordance with one embodiment of the present patent application.
Figure 7:
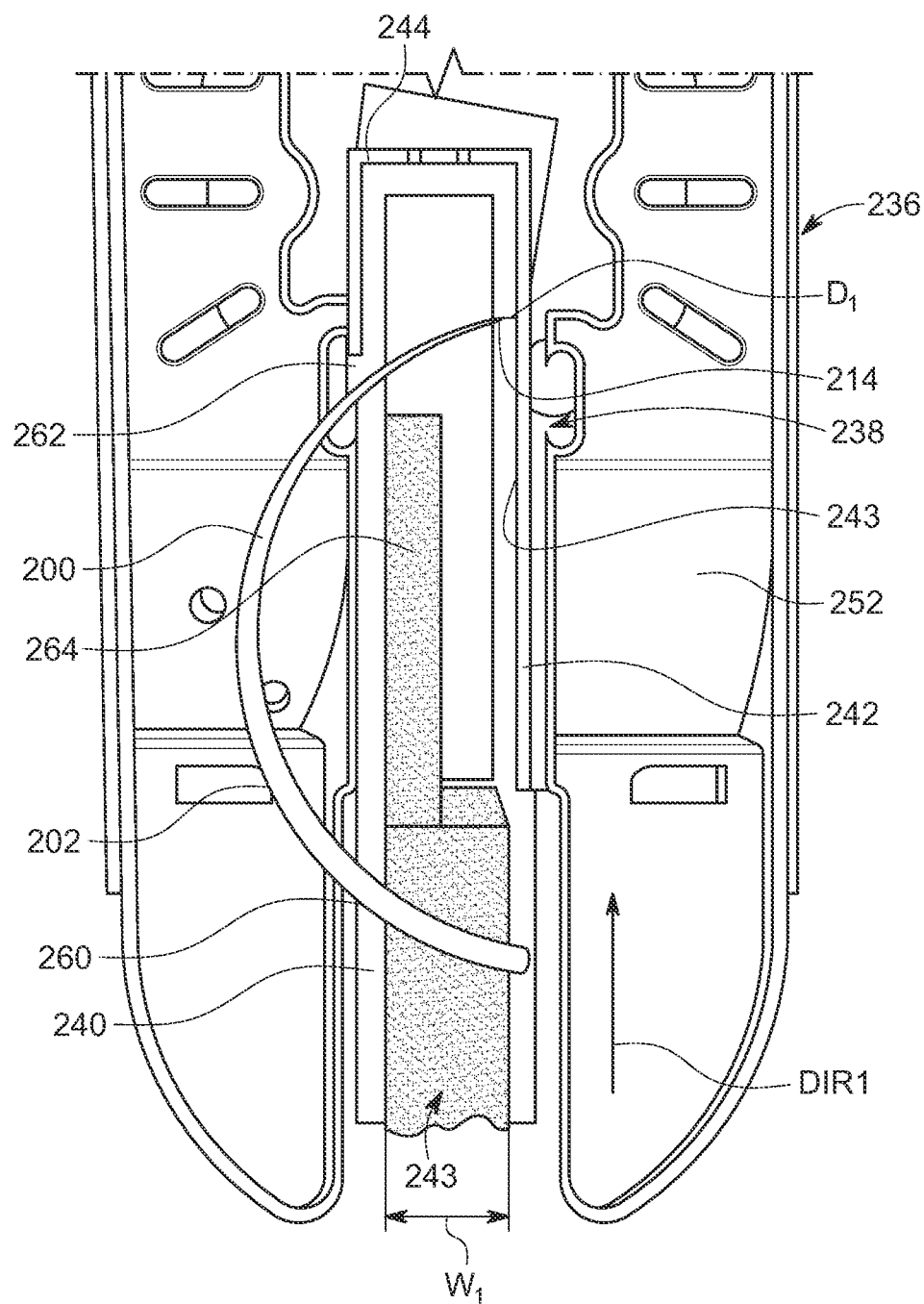
FIG. 7 is a magnified view of the suture needle package and the needle driver alignment guide of FIG. 6.

Referring to FIGS. 6 and 7, in one embodiment, a suture needle package 236 preferably includes a base 250 having a top surface 252 that is adapted to secure a suture needle 200 over the top surface 252. In one embodiment, the suture needle package 236 preferably has a proximal end 254, a distal end 256, and a longitudinal axis $A_2$ that desirably extends from the proximal end 254 to the distal end 256 of the package. In one embodiment, the suture needle package 236 desirably includes a needle driver alignment guide 238 that preferably extends along the longitudinal axis $A_2$ of the base of the suture needle package 236. In one embodiment, the needle driver alignment guide desirably includes a first lateral guide wall 240, a second lateral guide wall 242 that opposes the first lateral guide wall 240, and an end wall 244 that preferably functions at a hard stop for halting distal movement of a needle driver through the needle driver alignment guide 238. The first and second lateral guide walls and the end wall preferably define the boundaries of a needle driver guide channel 243 provided on the suture needle package. In one embodiment, the needle driver alignment guide 238 defines a width $W_2$ that extends laterally between opposing inner surfaces of the first lateral guide wall 240 and the second lateral guide wall 242. The width $W_2$ preferably equals the distance between inner surfaces of the first and second lateral guide walls 240, 242.

In one embodiment, the suture needle 200 is secured over a top of the suture needle package 236 so that the tip 214 at a distal-most end of the suture needle 200 is positioned between the first lateral guide wall 240, the second lateral guide wall 242, and the end wall 244 that functions as a hard stop. In one embodiment, when the suture needle 200 is secured to the suture needle package 236, a gap G is present between the tip 214 and the inner surface of the second lateral guide wall 242. In one embodiment, the tip 214 is preferably spaced away from the inner surface 245 (FIG. 7) of the second lateral guide wall 242 by a distance that is preferably less than ½ the distance defined by the width $W_2$ of the needle driver alignment guide. The tip 214 is spaced proximally from the end wall 244 by a distance $L_3$ Referring to FIG. 7, in one embodiment, the suture needle package 236 preferably includes a proximal connector 260 that releasably secures a proximal section of the suture needle 100 over the top surface 252 of the suture needle package, and a distal connector 262 that preferably secures a distal section of the suture needle 200 over the top surface 252 of the suture needle package 236. The proximal and distal connectors 260, 262 preferably form a releasable, friction fit, and/or snap-fit connection with the elongated body 202 of the suture needle 200 so that the suture needle 200 may be selectively detached and removed from the suture needle package 236. The proximal and distal connectors 260, 262 desirably hold the suture needle 100 in place within the package and prevent the suture needle from shifting or being loose during initial packaging, shipment, and storage of the suture needle.

The needle driver alignment guide 238 preferably includes the end wall 244 that interconnects distal ends of the respective first and second lateral guide walls 240, 242. The end wall 244 preferably functions as a hard stop for abutting against a distal-most end of the needle driver as the needle driver is advanced through the needle driver alignment guide 238 in the direction DIR1. In one embodiment, as the needle driver 116 is advanced through the needle driver alignment guide 238 in the direction DIR1, when a distal end of the lower jaw of the needle driver abuts against the end wall 244, the top surface of the lower jaw is preferably aligned with the tip 214 of the suture needle 200 and the bottom surface of the upper jaw is also preferably aligned with and overlies the tip of the suture needle. The suture needle guide channel 238 preferably has depth that aligns the lower jaw below the tip 214 and the upper jaw above the tip.

In one embodiment, the suture needle package 236 may include a resilient element 264 (e.g., a foam strip, one or more springs) that desirably abuts against a side of the elongated shaft of the needle driver 116 (FIG. 2A) for pressing the elongated shaft against the inner surface 243 of the second lateral guide wall 242, which insures that the opposing top and bottom surfaces of the respective lower and upper jaws of the clamping assembly remain aligned with the tip 214 of the suture needle 200. In one embodiment, the resilient element 264 may be a strip of foam that is adapted to press against a lateral side of the elongated shaft of the needle driver for urging the elongated shaft and the clamping assembly to abut against the second lateral guide wall 242. In one embodiment, the resilient element 264 may include one or more springs that press against a lateral side of the elongated shaft of the needle driver.

Figure 8A:
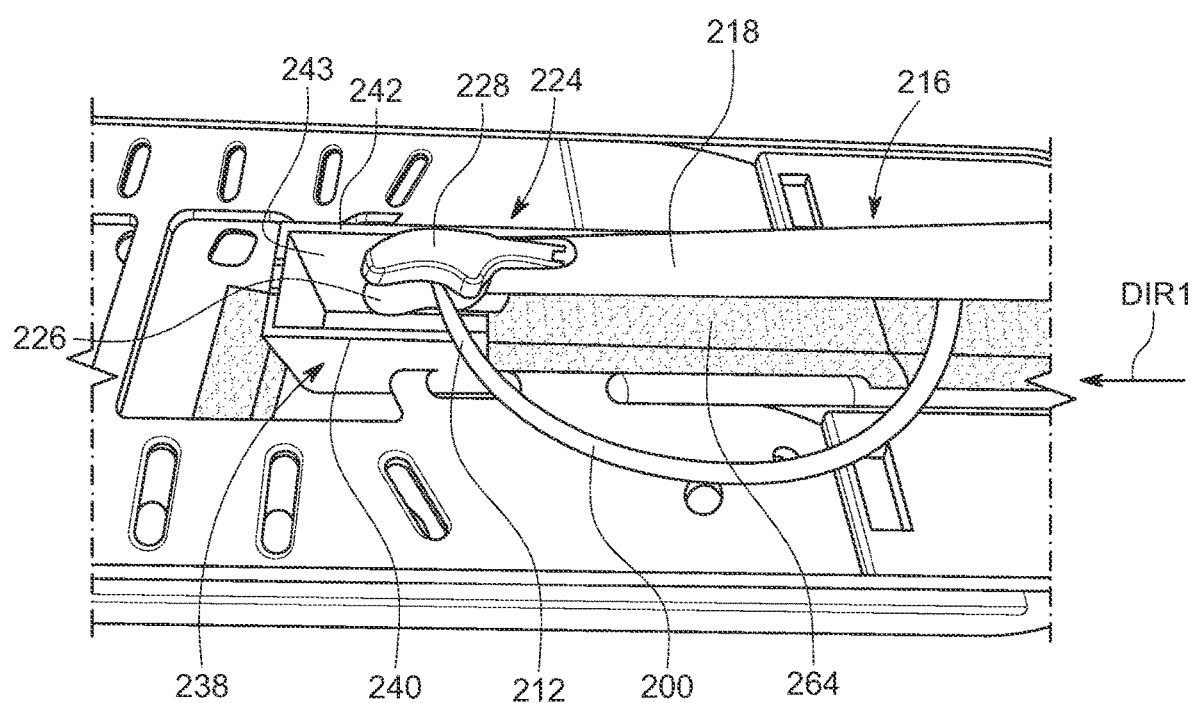
FIG. 8A shows the clamping assembly of the needle driver of FIGS. 2A and 2B in a closed position for securing the tip of a suture needle, in accordance with one embodiment of the present patent application.

Referring to FIG. 8A, in one embodiment, the elongated shaft 218 of the needle driver 216 is preferably advanced through the needle driver alignment guide 238 in the direction DIR1 for engaging the tip 214 (FIG. 7) located at the distal-most end of the suture needle 200. The resilient element 264 positioned between the first and second lateral guide walls 240, 242 of the needle driver alignment guide 238 desirably urges the elongated shaft 218 against the inner surface 243 of the second lateral guide wall 242 so that the clamping assembly 224 is aligned with the tip 214 (FIG. 7) at the distal-most end of the suture needle 200. When the tip of the suture needle is positioned between the lower jaw 226 and the upper jaw 228 of the clamping assembly 224, the clamping assembly 224 may be closed for pinching the tapered section 212 of the suture needle 200 between the opposing top and bottom surfaces of the respective lower and upper jaws 226, 228.

Figure 8B:
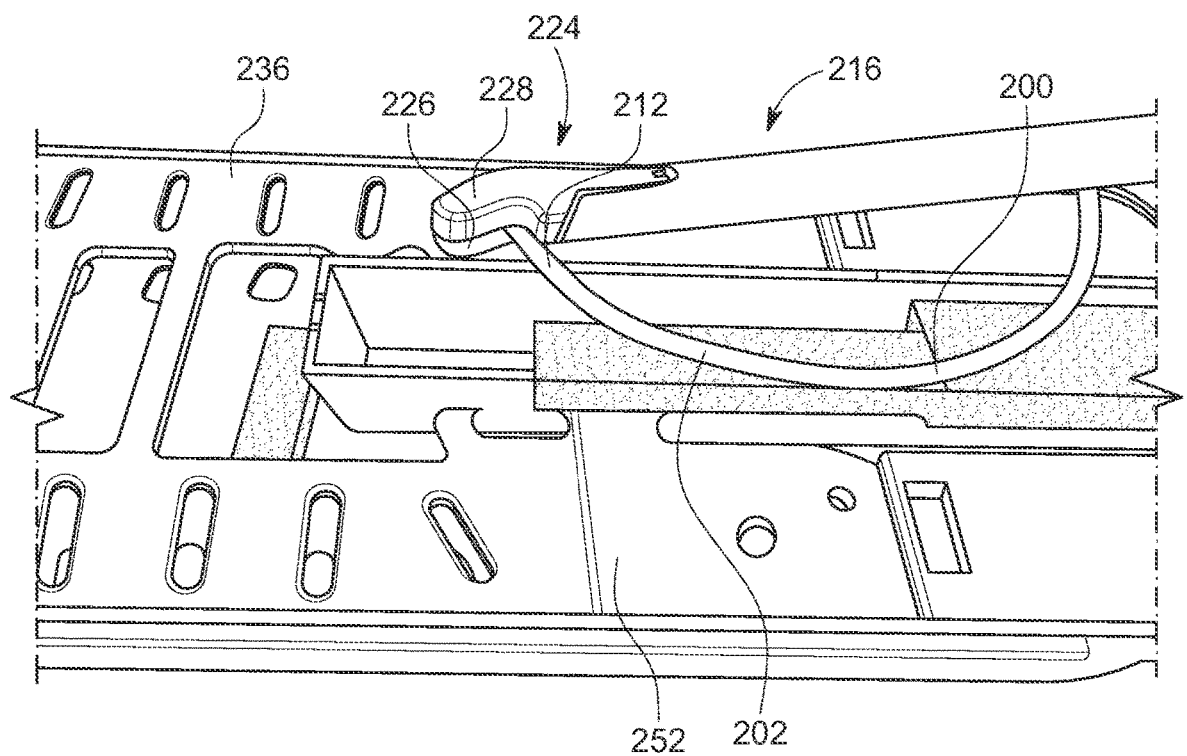
FIG. 8B shows the needle driver of FIG. 8A removing the suture needle from the suture needle package, in accordance with one embodiment of the present patent application.

Referring to FIG. 8B, in one embodiment, after the clamping assembly 224 of the needle driver 216 has been closed for engaging the tapered section 212 of the suture needle 200 between the lower jaw 226 and the upper jaw 228, the tip 214 (FIG. 7) of the suture needle is preferably surrounded by the lower and upper jaws of the clamping assembly so that the tip is not exposed outside the perimeter of the lower and upper jaws. The clamped suture needle 200 may be lifted away from the top surface 252 of the suture needle package 236 for uncoupling the elongated body 202 from the proximal and distal connectors 260, 262 (FIG. 7) provided on the top surface 252 of the suture needle package 236.

Figure 9A:
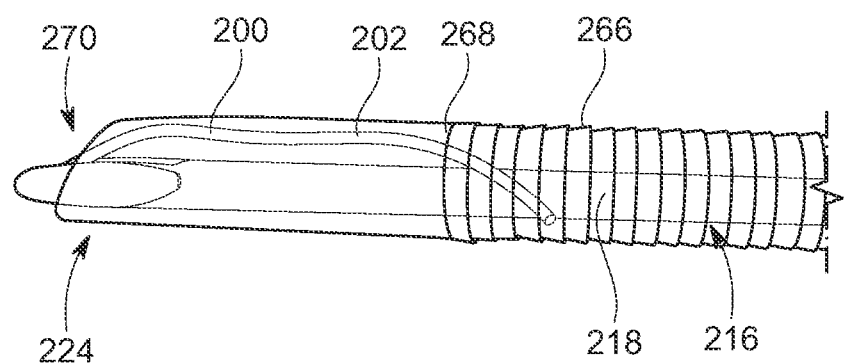
FIG. 9A shows a stage of a method of using a needle driver to advance an elastic suture needle toward a distal end of a trocar, in accordance with one embodiment of the present patent application.

Referring to FIG. 9A, in one embodiment, after the clamping assembly 224 of the needle driver 216 has been closed for clamping onto the tapered section of the suture needle 200, the needle driver 216 may be utilized for advancing the suture needle 200 through a trocar for positioning the suture needle at a surgical site for performing a suturing operation. In one embodiment, a trocar 266 preferably has an elongated conduit 268 defining an inner diameter that extends to an opening at a distal end 270 of the trocar. The clamping assembly 224 of the needle driver 216 is preferably advanced through the conduit 268 of the trocar 266 for pulling the needle 200 through the trocar. As the suture needle 200 is pulled by the clamping assembly 224 toward the distal end 270 of the trocar 266, the elongated body 202 of the superelastic suture needle 200 preferably elastically deforms (e.g., straightens out, becomes flatter) as shown in FIG. 9A.

Figure 9B:
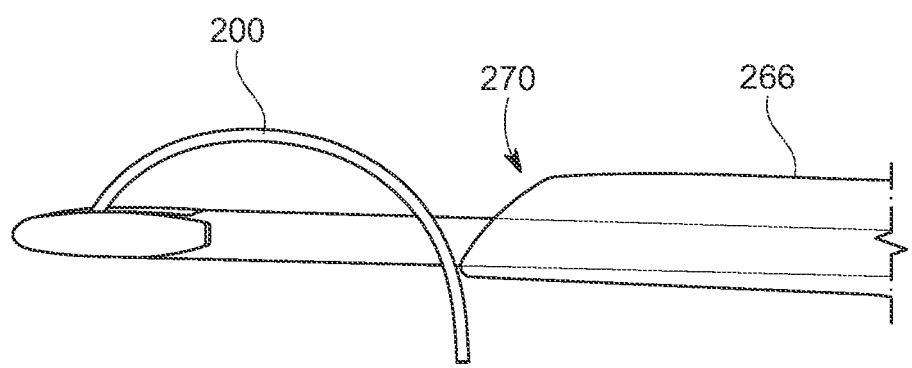
FIG. 9B shows the needle driver and the elastic suture needle of FIG. 9A after the suture needle has been advanced beyond the distal end of the trocar for being located at a surgical site, in accordance with one embodiment of the present patent application.

Referring to FIG. 9B, after the clamped suture needle 200 has been advanced beyond the distal end 270 of the trocar 266, the elastic suture needle 200 preferably returns to the original curved configuration (e.g., a half circle shape). Surgical personnel may then utilize the curved suture needle 200 for performing a suturing operation at the surgical site.

Figure 9C:
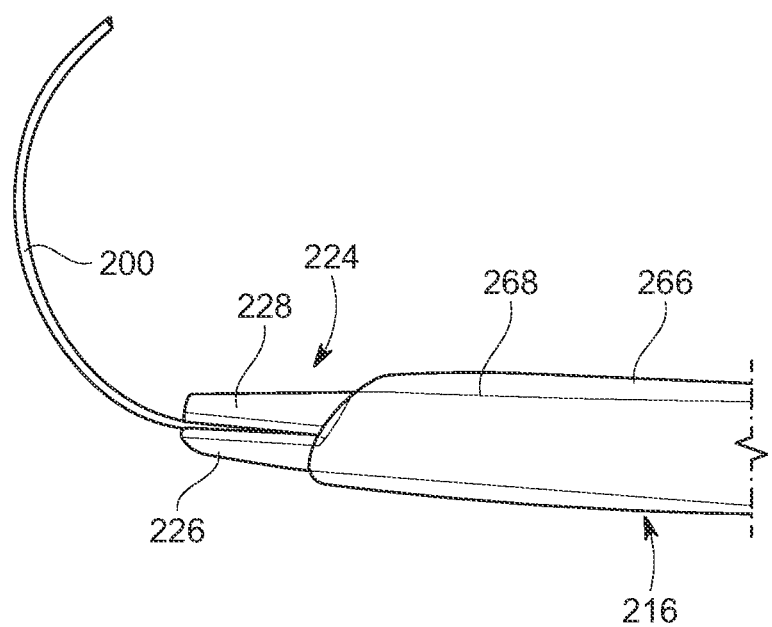
FIG. 9C shows a stage of a method of using a needle driver to retract an elastic suture needle from a surgical site and toward a proximal end of the trocar, in accordance with one embodiment of the present patent application.

Referring to FIG. 9C, in one embodiment, at the conclusion of a suturing operation, the suture needle 200 may be removed from a patient by retracting the suture needle through the trocar 260. In one embodiment, the clamping assembly 224 is again closed for securing the tip of the curved suture needle 200 between the lower jaw 226 and the upper jaw 228 of the needle driver 216.

Figure 9D:
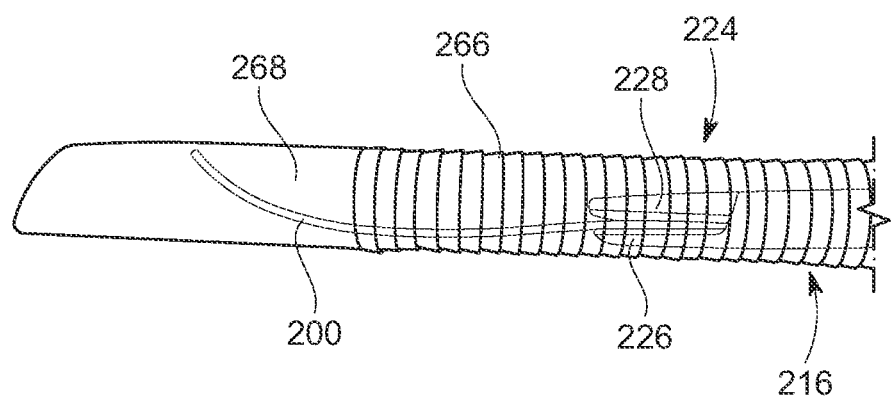
FIG. 9D shows a later stage of a method of retracting the elastic suture needle toward the proximal end of the trocar, in accordance with one embodiment of the present patent application.
Figure 10A:
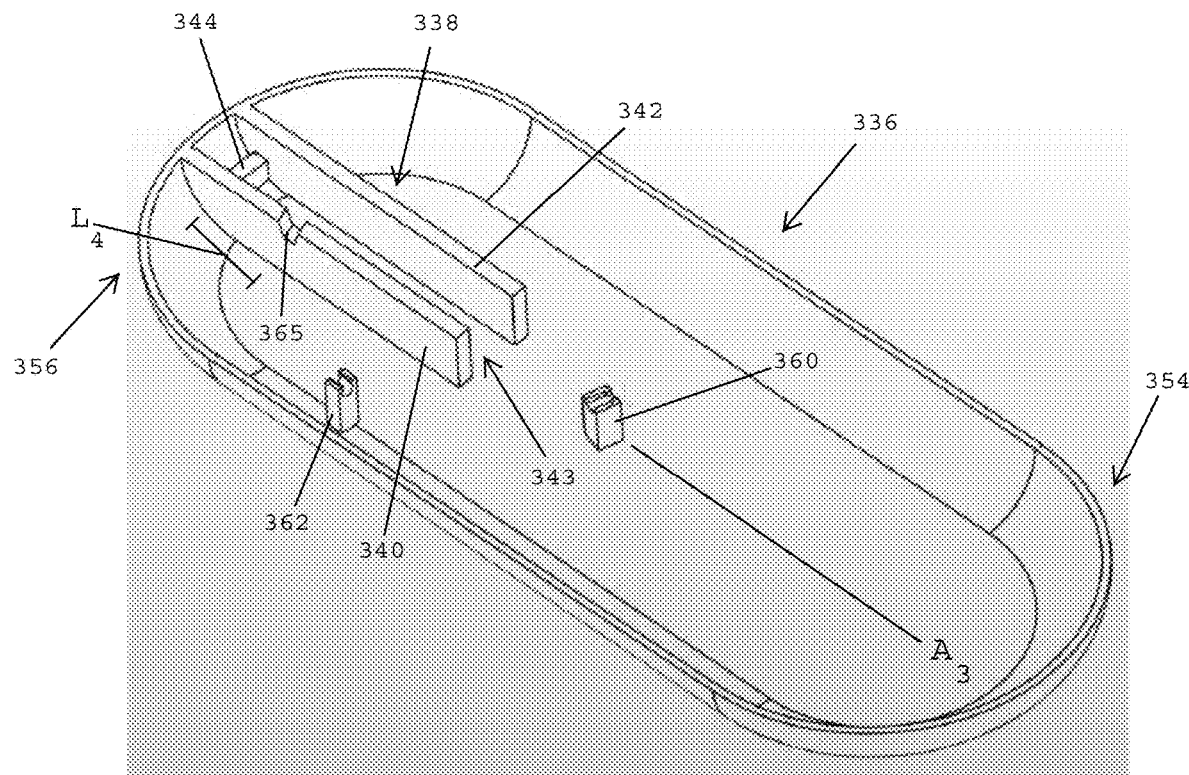
FIG. 10A is a perspective view of a suture needle package having a needle driver alignment guide, in accordance with one embodiment of the present patent application.
Figure 10B:
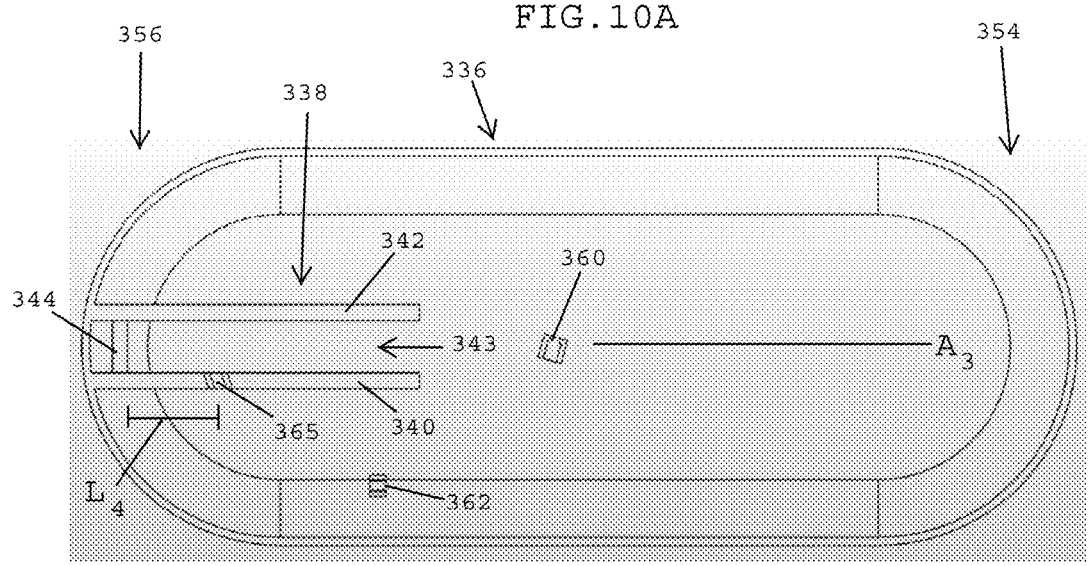
FIG. 10B is a top plan view of the suture needle package shown in FIG. 10A.
Figure 10C:
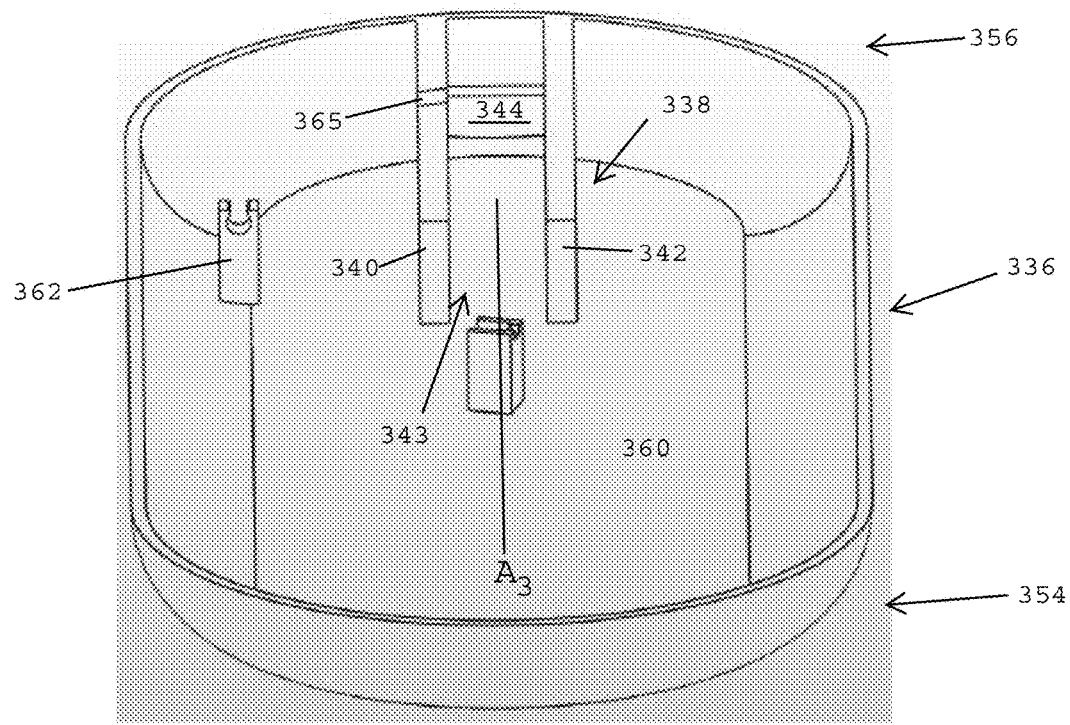
FIG. 10O is a perspective end view of the suture needle package shown in FIGS. 10A and 10B.
FIG. 10D is another perspective view of the suture needle package shown in FIGS. 10A-10C.
Figure 10D:
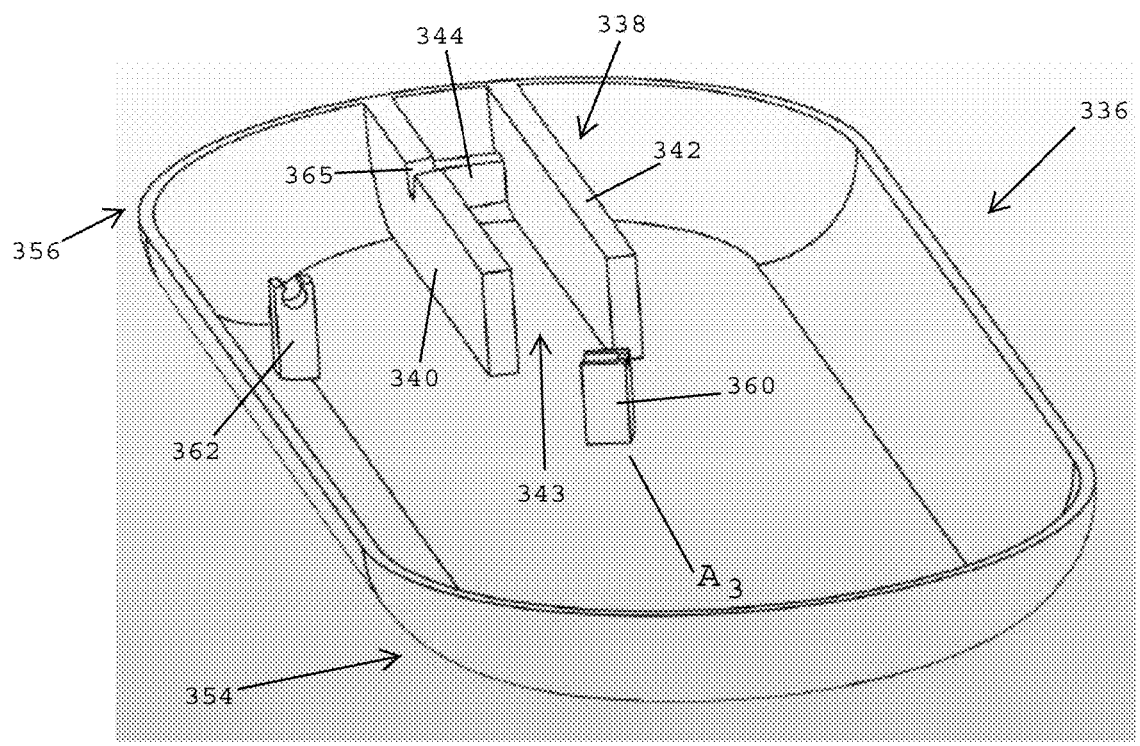
Figure 11A:
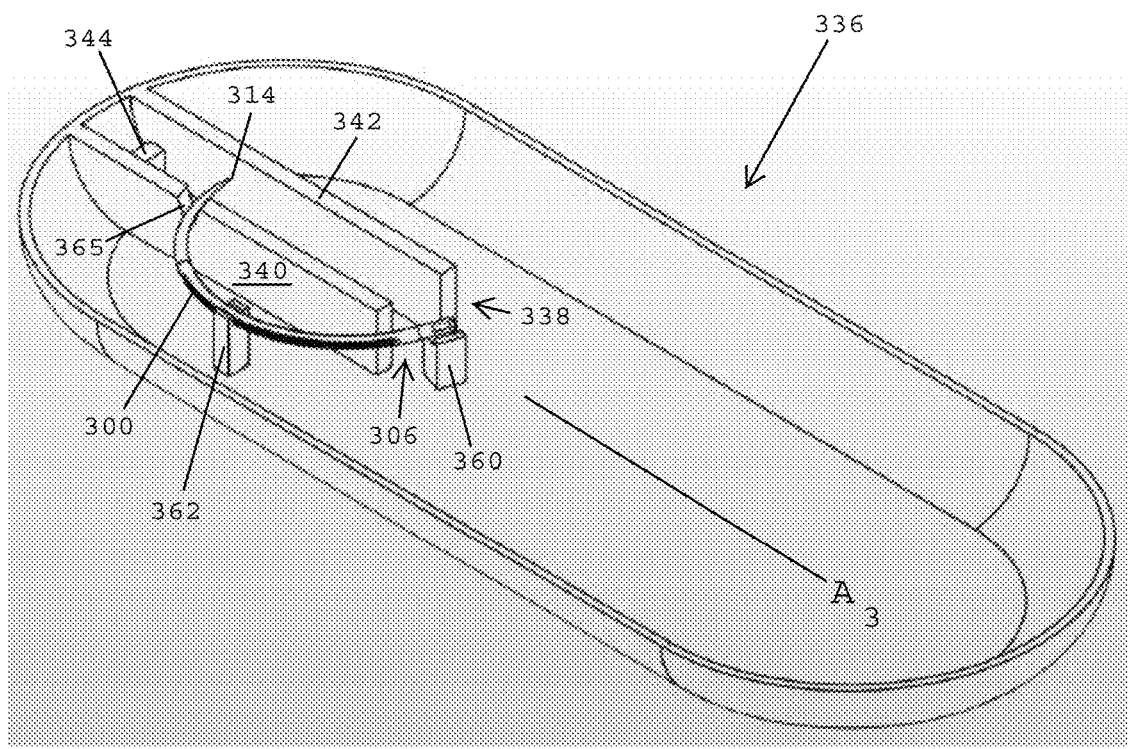
FIG. 11A is a perspective view of the suture needle package of FIGS. 10A-10D and a suture needle secured to the suture needle package, in accordance with one embodiment of the present patent application.
Figure 11B:
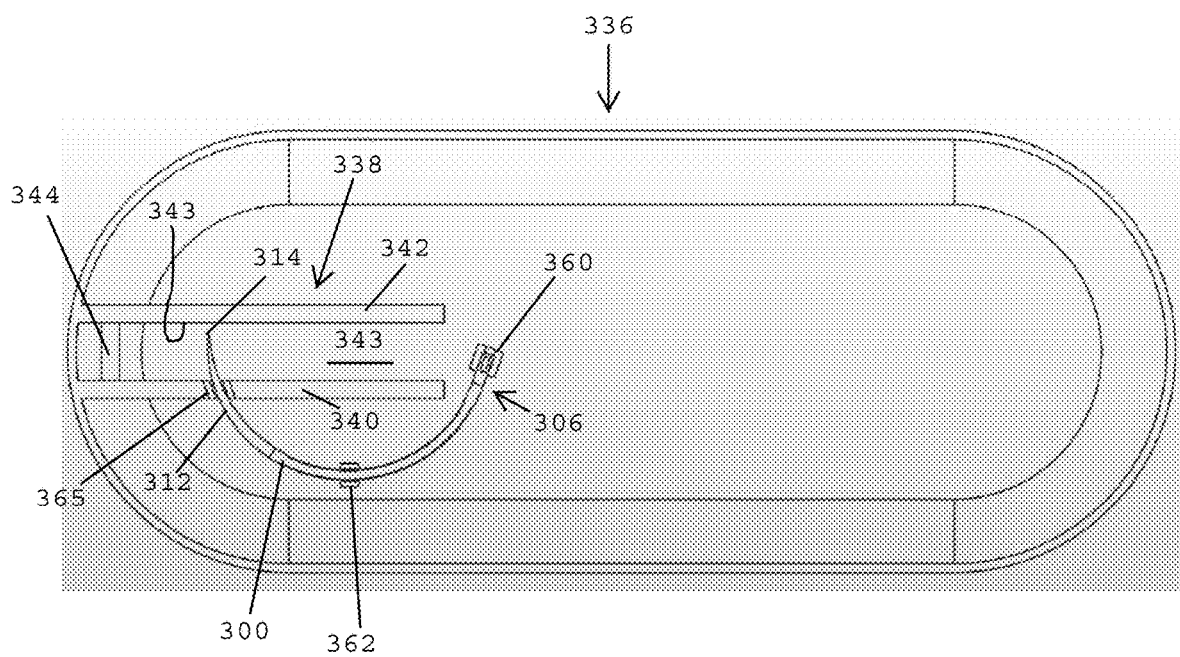
FIG. 11B is a top plan view of the suture needle package and the suture needle shown in FIG. 11A.
Figure 11C:
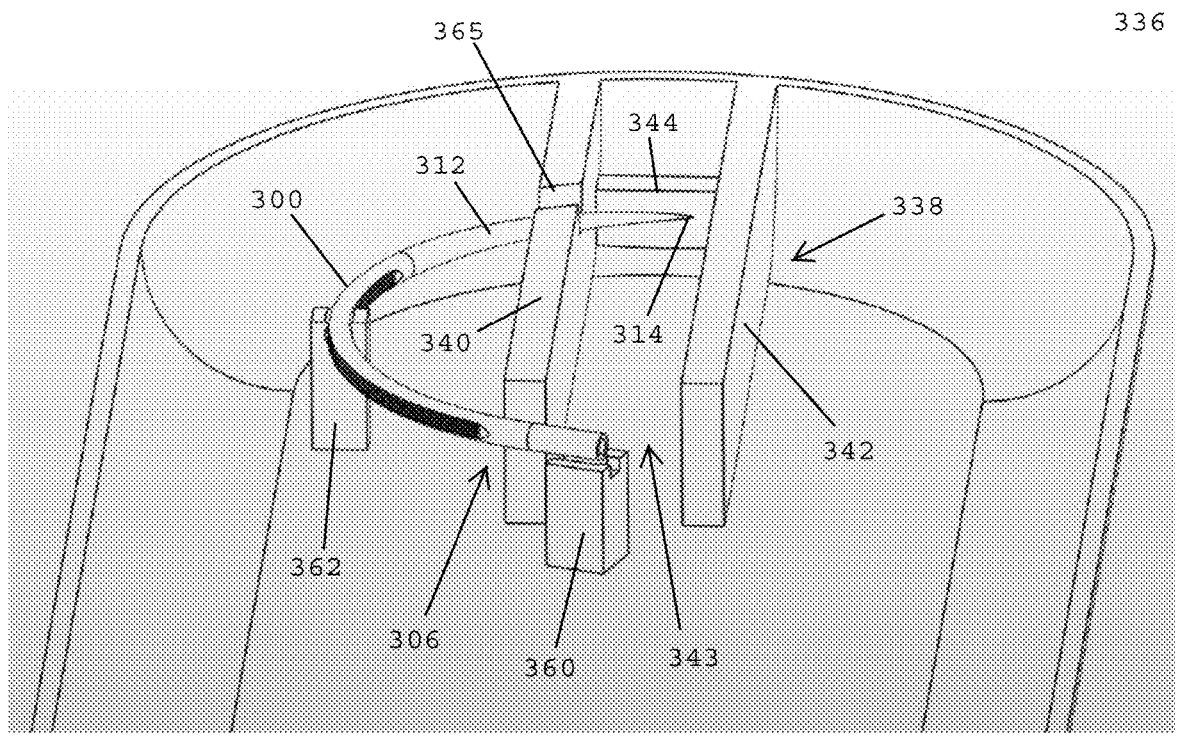
FIG. 11C is a perspective end view of the suture needle package and the suture needle shown in FIGS. 11A and 11B.
Figure 11D:
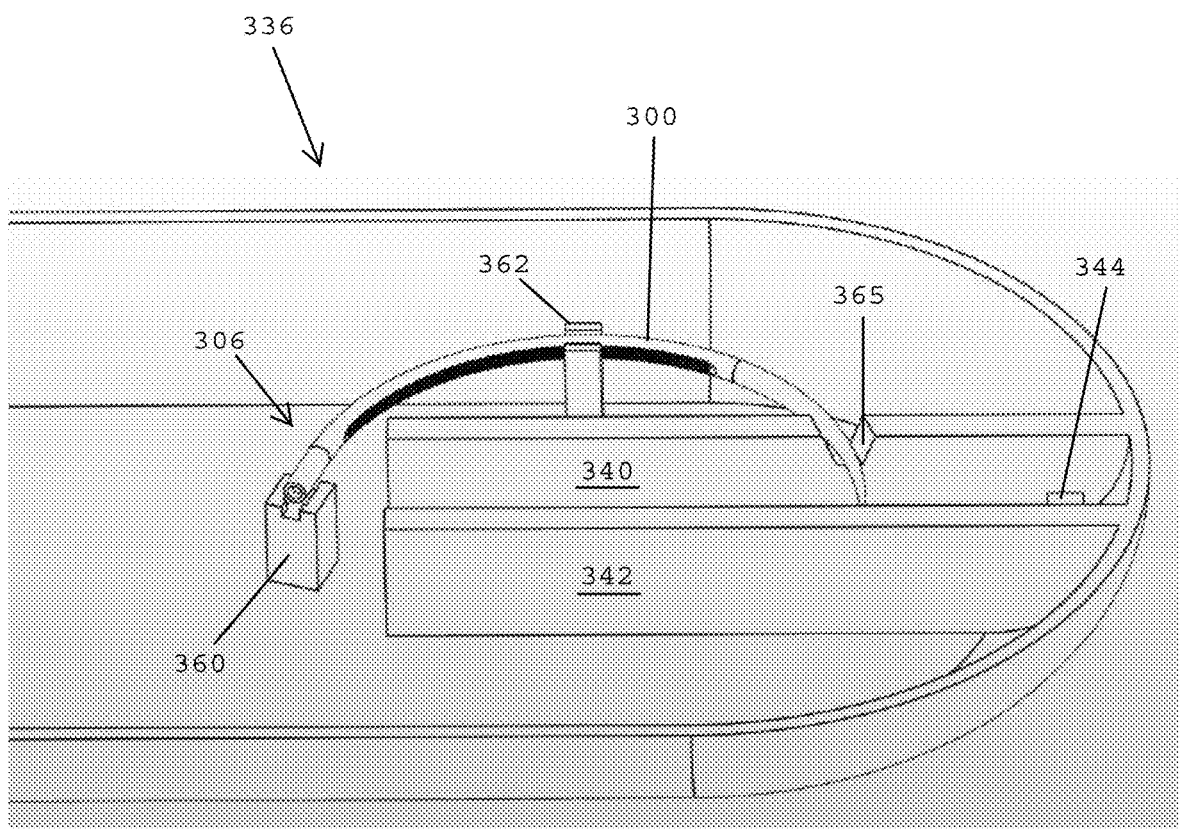
FIG. 11D is a magnified view of a distal end of the suture needle package and the suture needle shown in FIGS. 11A-11C.

Referring to FIG. 9D, in one embodiment, the suture needle 200 is retracted through the cannula 268 of the trocar 266. The superelastic suture needle 200 preferably straightens out as it is retracted through the trocar by the clamping assembly 224 of the needle driver 216. As the superelastic suture needle is withdrawn through the trocar 266, the lower and upper jaws 226, 228 preferably engage the tapered section of the suture needle 200 and surround the tip.

Referring to FIGS. 10A-10D, in one embodiment, a suture needle package 336 adapted to hold at least one suture needle preferably has a proximal end 354, a distal end 356 and a longitudinal axis $A_3$ that extends along the length of the suture needle package 336 between the proximal end 354 and the distal end 356. In one embodiment, the suture needle package 336 preferably includes a needle driver alignment guide 338 that extends along the longitudinal axis $A_3$ of the suture needle package 336. In one embodiment, the needle driver alignment guide 338 preferably includes a first lateral guide wall 340 and an opposing second lateral guide wall 342 that desirably define a needle driver guide channel 343 for guiding advancement of a needle driver toward the distal end 352 of the suture needle package 336. In one embodiment, the needle driver alignment guide 338 preferably includes an end wall 344 that functions as a hard stop for halting distal movement of the jaws of a needle driver through the needle driver alignment channel. In one embodiment, the suture needle package 336 preferably includes a proximal connector 360 that is adapted to form a releasable connection with a proximal end of a suture needle, and a lateral connector 362 that is adapted to form a releasable connection with a more distal section of the suture needle. The suture needle package 336 also preferably includes a securing notch 365 formed at an upper end of the first lateral guide wall 340 that is adapted to form a releasable connection with a tapered section of a suture needle. In one embodiment, the securing notch 365 is preferably spaced a distance $L_4$ from the end wall 344 of the needle driver alignment guide 338.

Referring to FIGS. 11A-11D, in one embodiment, a suture needle 300 may be secured to the suture needle package 336 so that the tip 314 of the suture needle 300 is positioned between the first and second lateral guide walls 340, 342 and the end wall 344 of the needle driver alignment guide 338. In one embodiment, the tip 314 of the suture needle 300 is spaced away from the inner face 343 of the second lateral guide wall 342 so that a gap G is present between the tip 314 and the second lateral guide wall 342. In addition, the tip 314 is preferably held proximal to the end wall 344 by a distance $L_4$. In one embodiment, the distance $L_4$ is preferably less than the length of the top surface of the lower jaw of the needle driver, and is more preferably equal to about one half of the length of the top surface of the lower jaw of the clamping assembly, which insures alignment of the top surface of the lower jaw with the tip of the suture needle.

In one embodiment, the proximal end 306 of the suture needle 300 is releasably secured to the proximal connecter 360 of the suture needle package 336. In one embodiment, a mid-section of the suture needle 300 is releasably secured to the lateral connector 362 of the suture needle package 336. In one embodiment, the tapered section 312 of the suture needle 300 is releasably secured to the securing notch 365 provided at the upper end of the first lateral guide wall 340 of the needle driver alignment guide 338. The securing notch 365 desirably holds the tip 314 of the suture needle 300 at a known location having X, Y, and Z coordinates.

Figure 12:
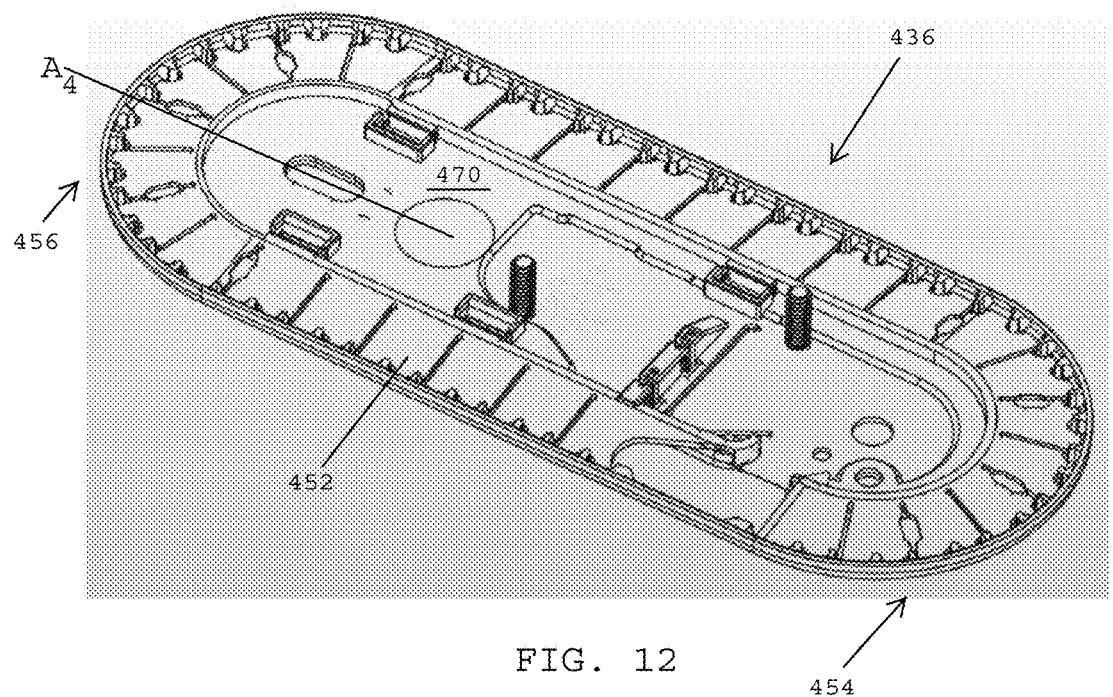
FIG. 12 is a perspective view of a base of a suture needle package, in accordance with one embodiment of the present patent application.

Referring to FIG. 12, in one embodiment, a suture needle package 436 preferably includes a base 452 having a proximal end 454, a distal end 456, and a longitudinal axis $A_4$ that extends from the proximal end 454 to the distal end 456 of the base 452. In one embodiment, the base 452 has a top surface 470 that is adapted to seat a needle driver alignment guide that holds a suture needle.

Figure 13A:
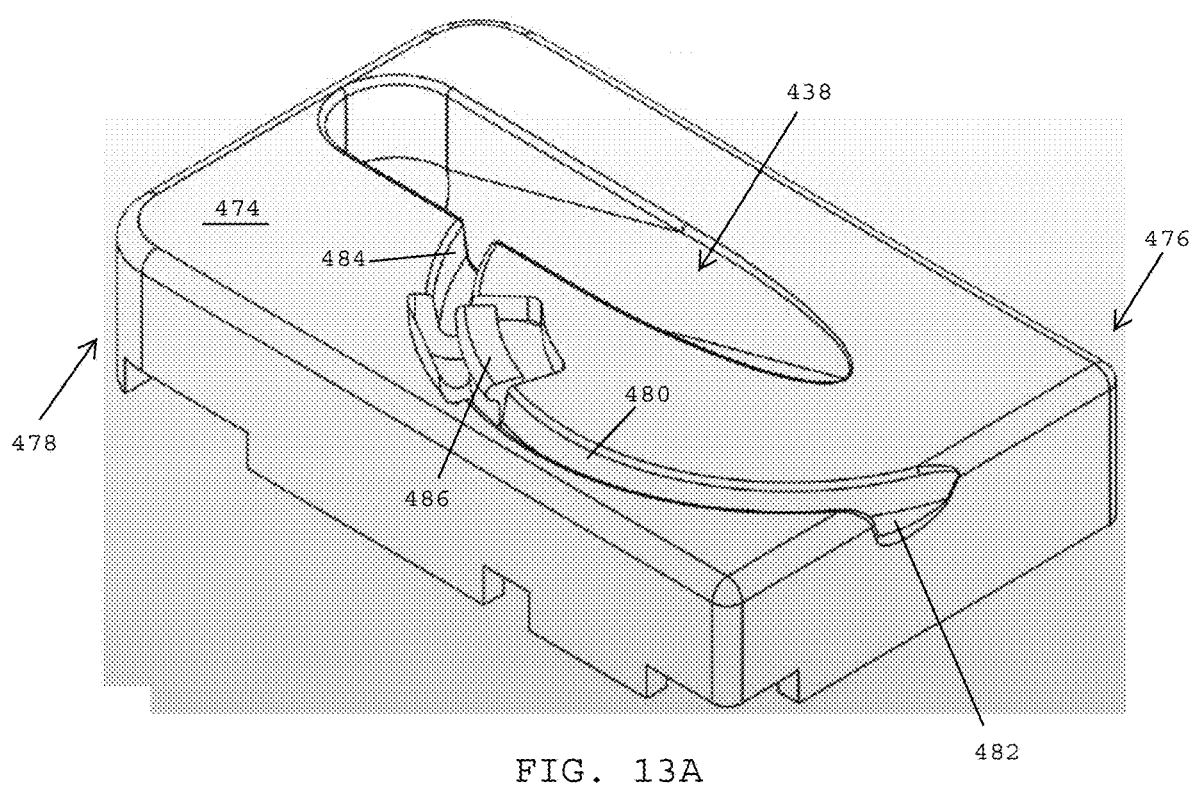
FIG. 13A is a perspective view of a needle driver alignment guide for a suture needle package, in accordance with one embodiment of the present patent application.
Figure 13B:
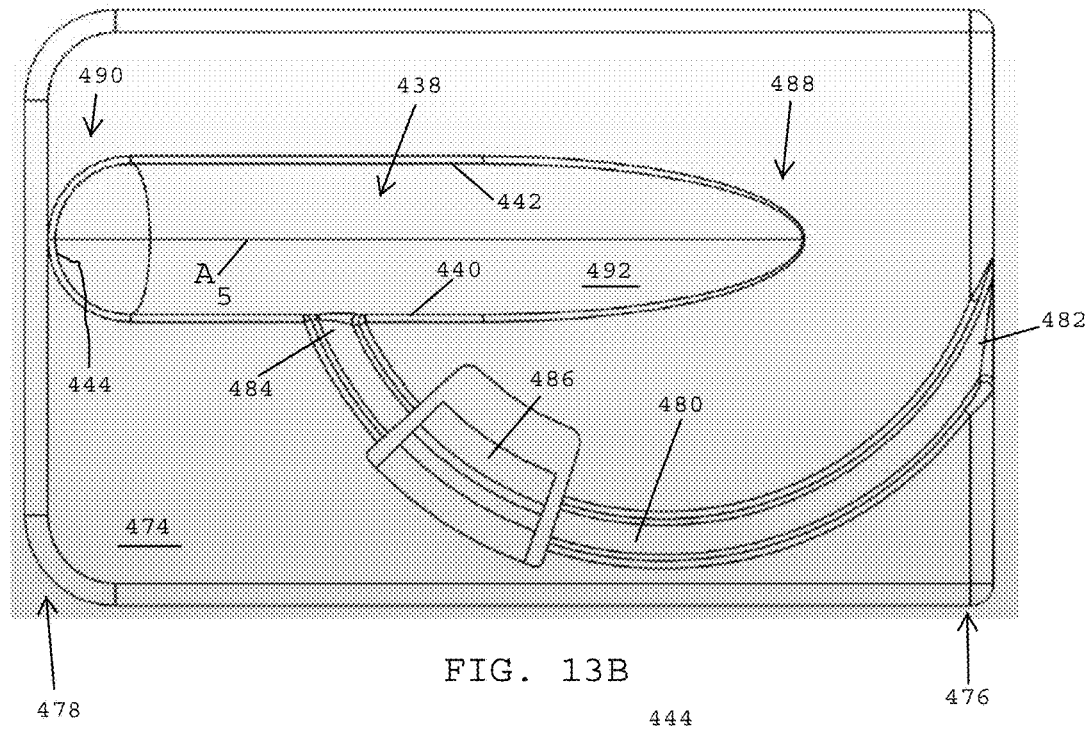
FIG. 13B is a top plan view of the needle driver alignment guide shown in FIG. 13A.
Figure 13C:
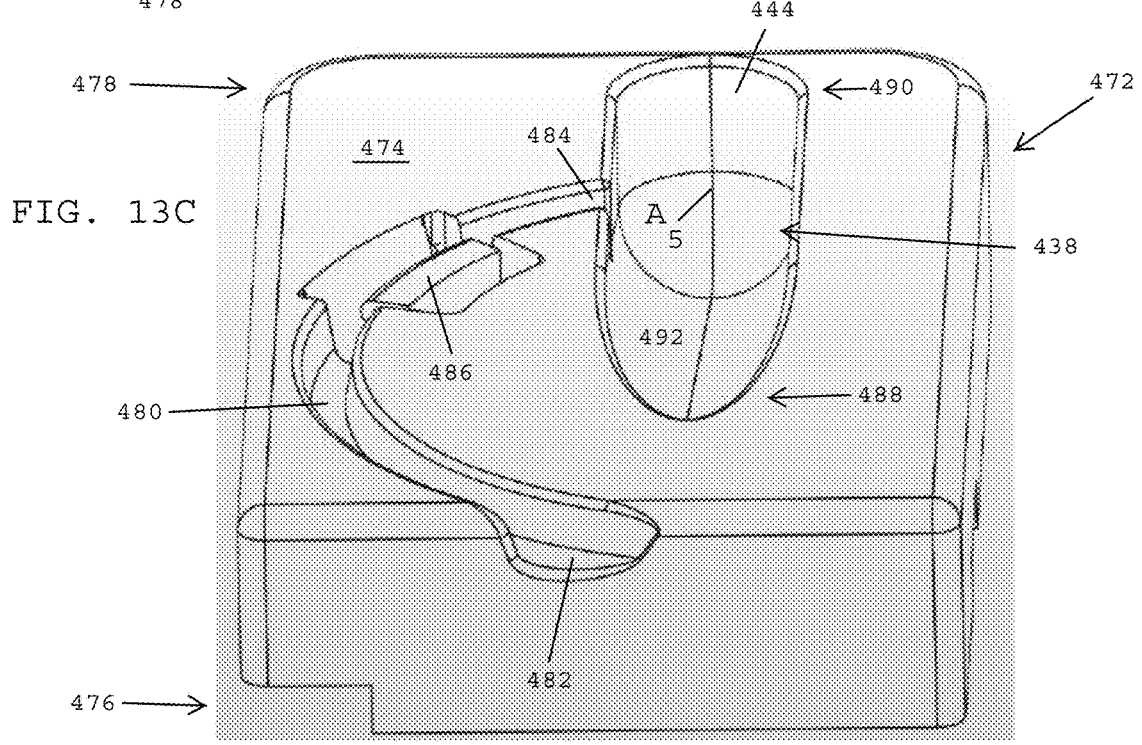
FIG. 13C is a perspective end view of the needle driver alignment guide shown in FIGS. 13A and 13B.
Figure 14A:
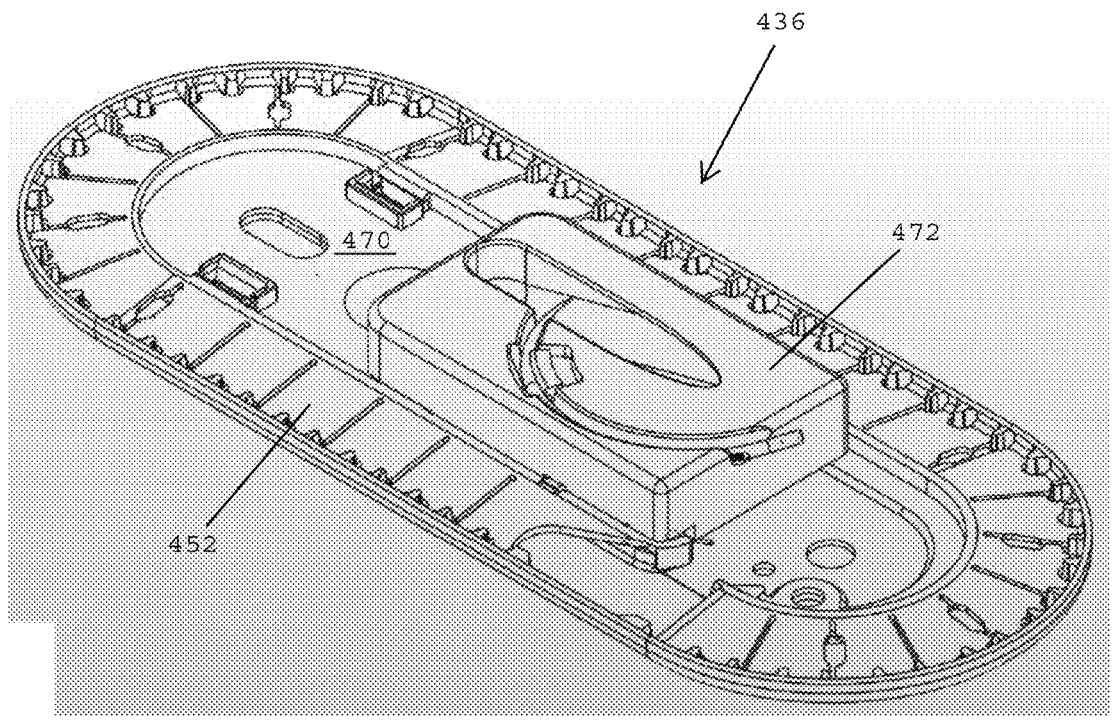
FIG. 14A shows the needle driver alignment guide of FIGS. 13A-13C secured atop the base of FIG. 12, with a suture needle secured over the needle driver alignment guide, in accordance with one embodiment of the present patent application.
Figure 14B:
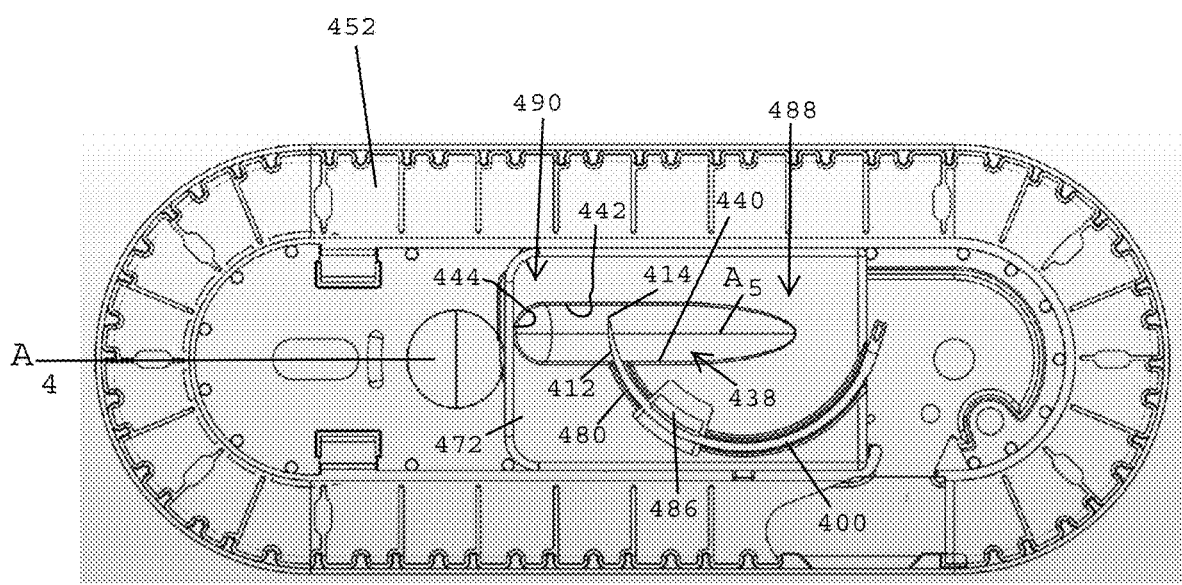
FIG. 14B is a top plan view of the base, the needle driver alignment guide, and the suture needle shown in FIG. 14A.
Figure 14C:
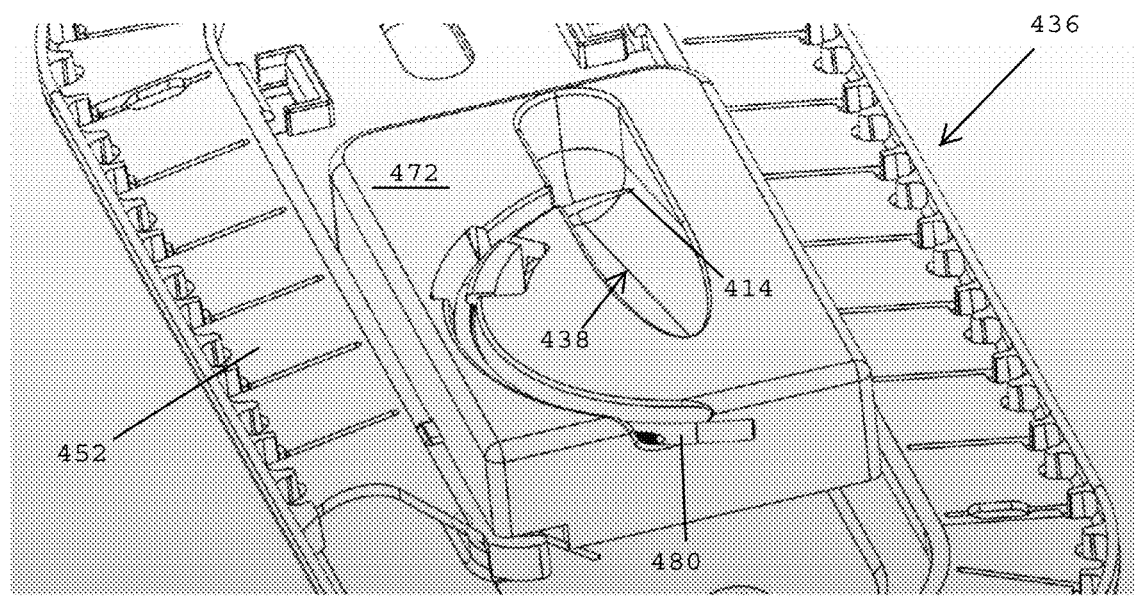
FIG. 14C is a magnified view of the needle driver alignment guide and the suture needle shown in FIGS. 14A and 14B.
Figure 14D:
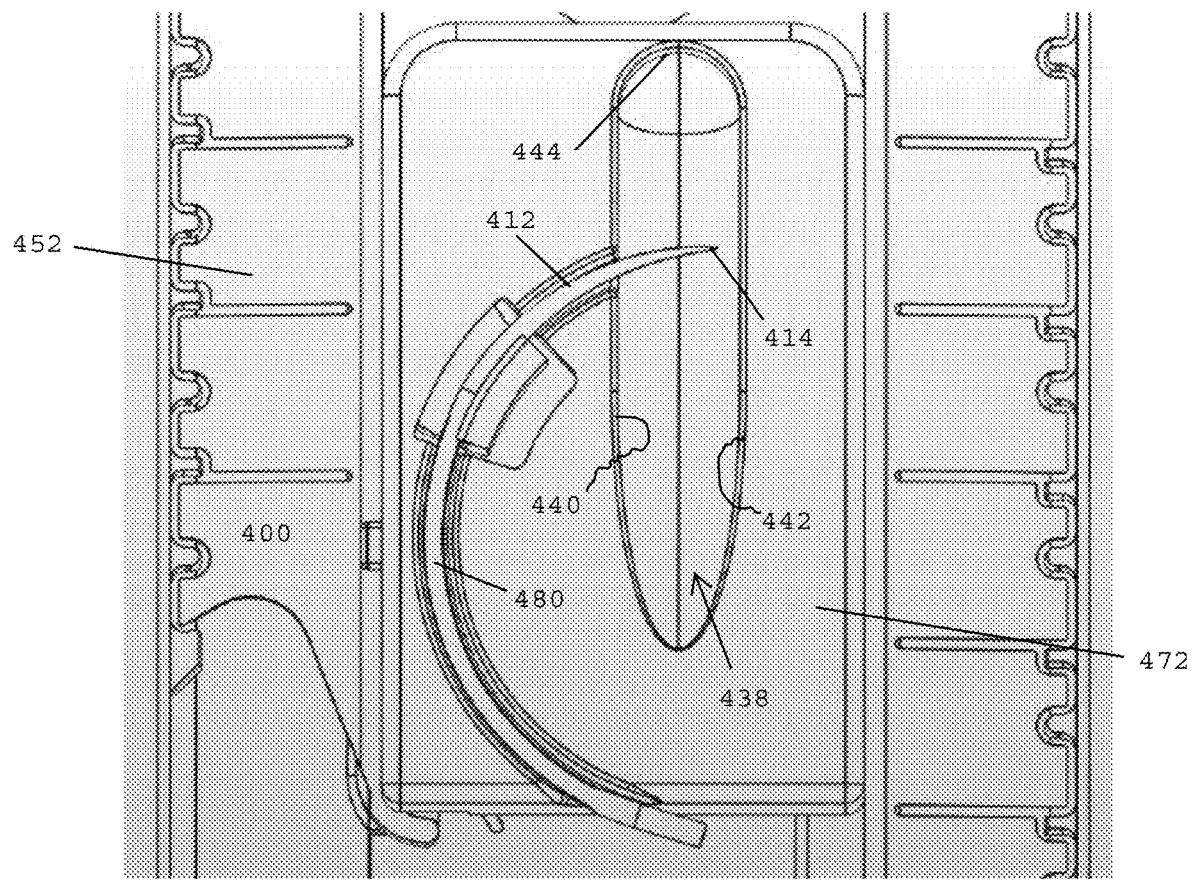
FIG. 14D is a top plan view of the needle driver alignment guide and the suture needle shown in FIG. 14C.

Referring to FIGS. 13A-13C, in one embodiment, a suture needle platform 472 preferably has a top surface 474 that extends from a proximal end 476 to a distal end 478 of the suture needle platform 472. In one embodiment, the suture needle platform 472 preferably includes a curved groove 480 that is adapted to receive and/or releasably secure a suture needle over the top surface 474 of the suture needle platform 472. In one embodiment, the curved groove 480 preferably has a proximal end 482 that is adapted to receive a proximal end of a curved suture needle and a distal end 484 that is adapted to receive a distal section of the curved suture needle. In one embodiment, the curved groove 480 preferably includes a resilient element 486 that is desirably adapted to engage the elongated body of a suture needle for releasably securing a curved suture needle within the curved groove 480 of the suture needle platform 472.

In one embodiment, the suture needle platform 472 preferably includes a needle driver alignment guide 438 that is formed in the top surface 474 of the suture needle platform 472. The needle driver alignment guide 438 preferably has a first lateral guide wall 440, an opposing second lateral guide wall 442, and an end wall 444 that functions as a hard stop at a distal-most end of the needle driver alignment guide.

Referring to FIGS. 13B and 13C, in one embodiment, the needle driver alignment guide 438 preferably has a proximal end 488 that is located closer to the proximal end 476 of the suture needle platform 472 and a distal end 490 that is located at the end wall 444 of the needle driver alignment guide 438. The needle driver alignment guide 438 preferably includes a floor 492 that may slope downwardly from the top surface 474 toward the end wall 444. The needle driver alignment guide 438 preferably extends along a longitudinal axis $A_5$.

Referring to FIGS. 14A-14D, in one embodiment, the suture needle platform 472 is preferably assembled over the top surface 470 of the base 452 of the suture needle package 436. The longitudinal axis $A_5$ of the needle driver alignment guide 438 is preferably co-axial with and extends along the longitudinal axis $A_4$ of the base 452 of the suture needle package 436. A suture needle 400 is preferably secured within the curved groove 480 provided in the top surface 474 of the suture needle platform 472. The curved groove 480 preferably holds the tip 414 of the suture needle 400 within the needle driver alignment guide 438 so that the tip 414 is preferably spaced away from the second lateral guide wall 442 of the needle driver alignment guide 438, whereby a gap G is present between the tip 414 and the inner surface of the second lateral guide wall 442. In one embodiment, the tip 114 is desirably spaced proximally from the end wall 444 of the needle driver alignment guide 438 by a distance $L_5$.

In one embodiment, a distal end of the needle driver 116 (FIG. 2A) may be advanced from the proximal end 488 to the distal end 490 of the needle driver alignment guide 438 until a distal-most end of the clamping assembly abuts against the end wall 444 of the needle driver alignment guide 438. At this stage, the opposing top and bottom surfaces of the respective lower and upper jaws of the clamping assembly are preferably aligned with the tip 414 of the suture needle 400. The lower and upper jaws of the clamping assembly may be moved to the closed position for engaging (e.g., clamping) the tapered section 412 of the suture needle 400. The needle driver may be used to remove the clamped suture needle 400 from the resilient connection 486 of the suture needle platform 472, whereupon the suture needle 400 may be extracted from the curved groove 480 formed in the top surface 474 of the suture needle platform 472. The needle driver may be utilized for advancing (e.g., pulling) the clamped suture needle 400 through a trocar to deliver the suture needle at a surgical site for performing a suturing operation.

Figure 15A:
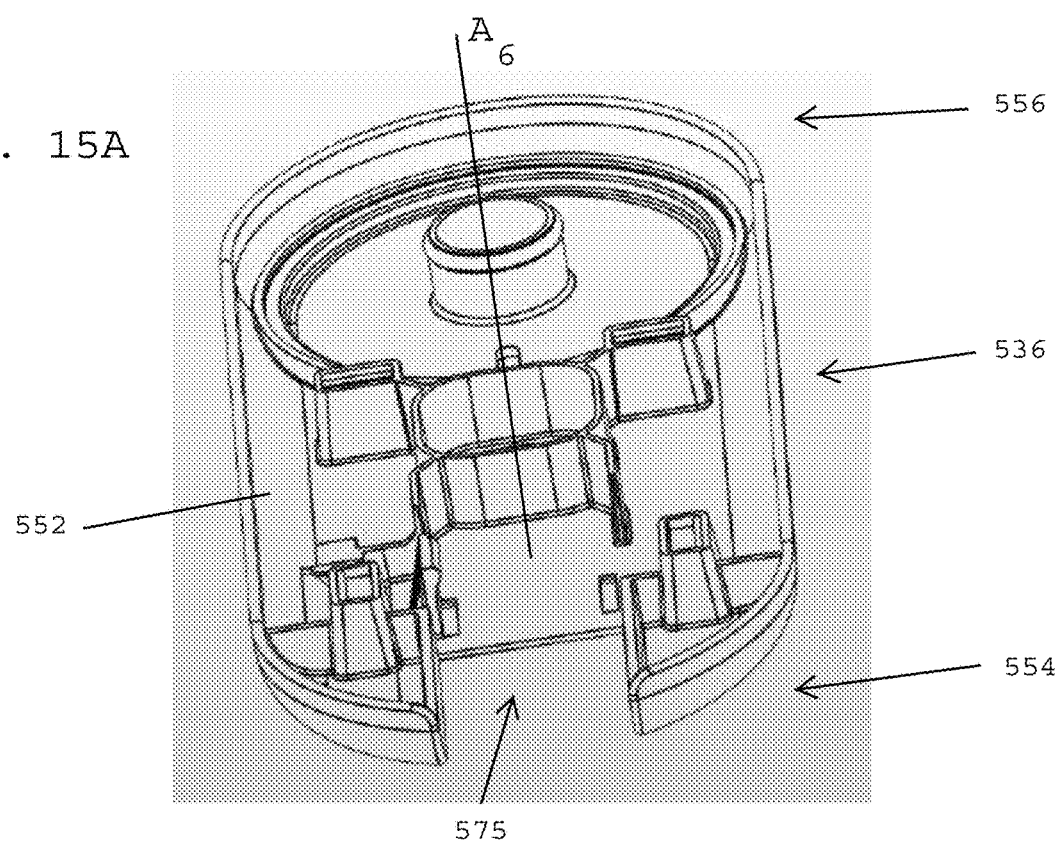
FIG. 15A is a perspective end view of a base of a suture needle package, in accordance with one embodiment of the present patent application.
Figure 15B:
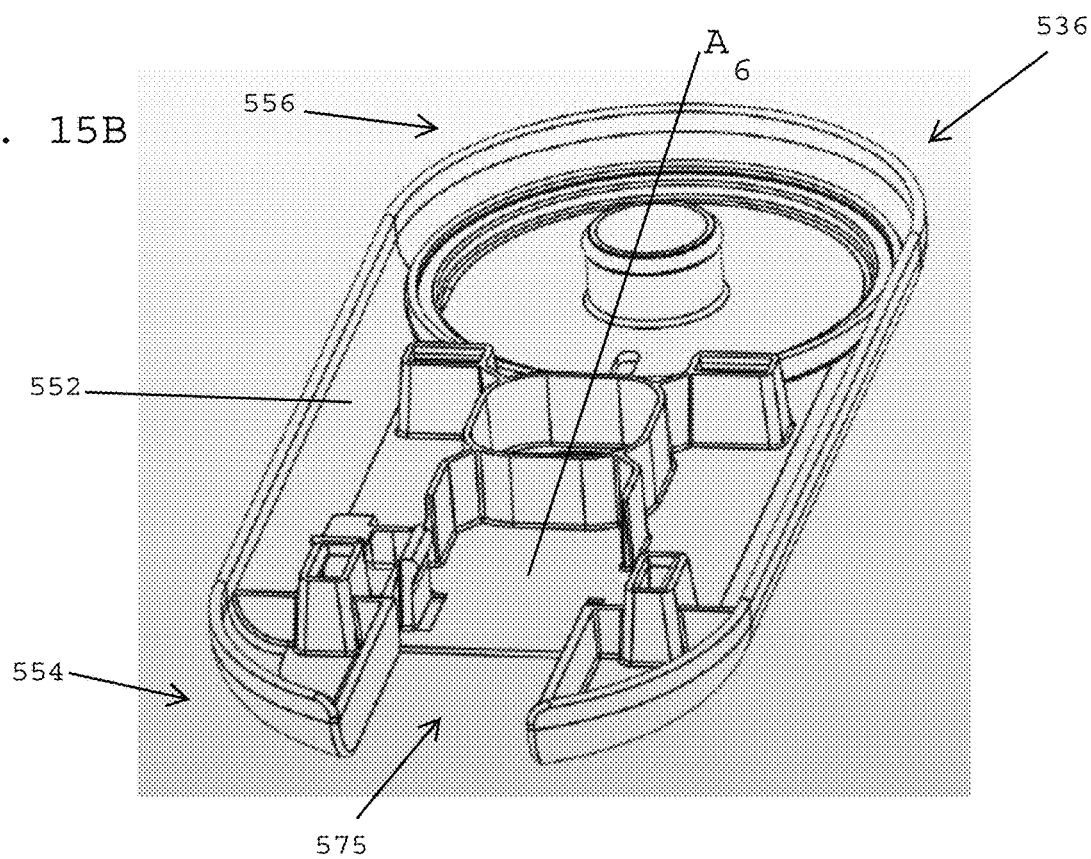
FIG. 15B is another perspective end view of the base of the suture needle package shown in FIG. 15A.

Referring to FIGS. 15A and 15B, in one embodiment, a suture needle package 536 preferably includes a base 552 having a proximal end 554, a distal end 556 and a longitudinal axis $A_6$ that extends from the proximal end 554 to the distal end 556. The base 552 may include a proximal gap 575 formed therein at the proximal end 554 of the base 552, which is adapted to receive a needle driver alignment guide, as will be described in more detail below.

Figure 16A:
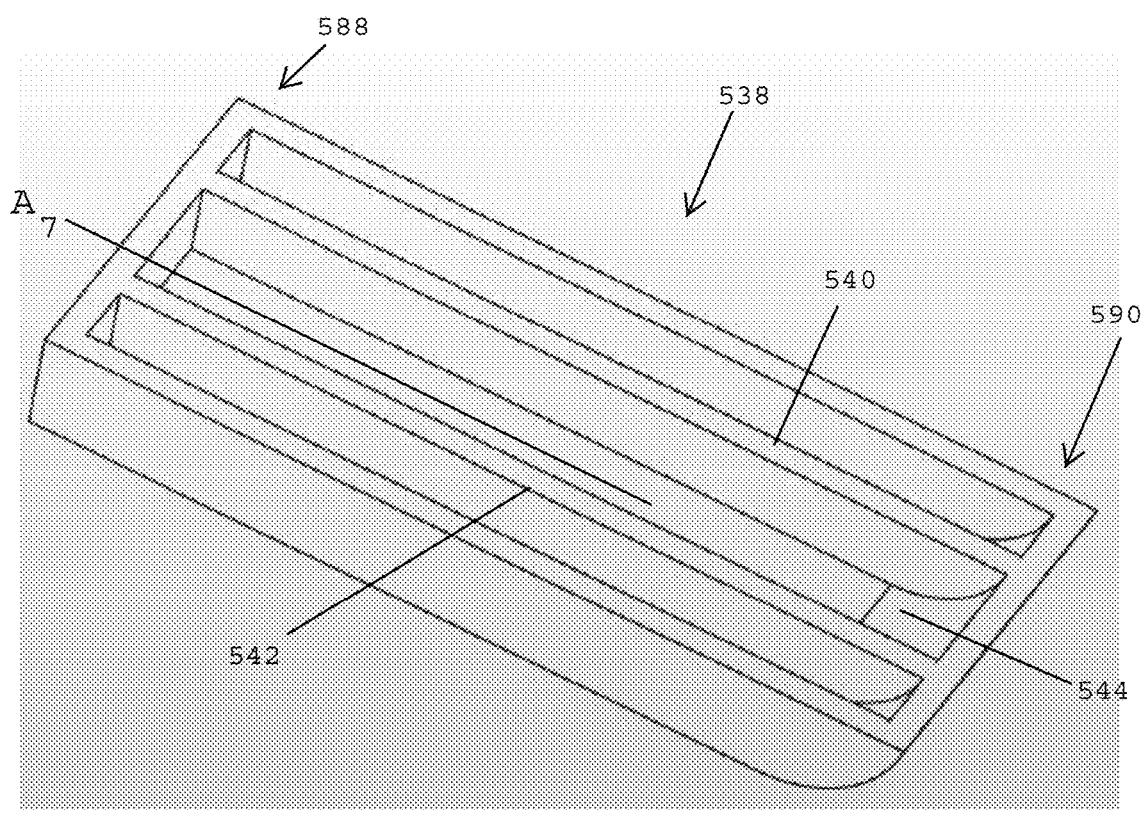
FIG. 16A is a perspective view of a needle driver alignment guide, in accordance with one embodiment of the present patent application.
Figure 16B:
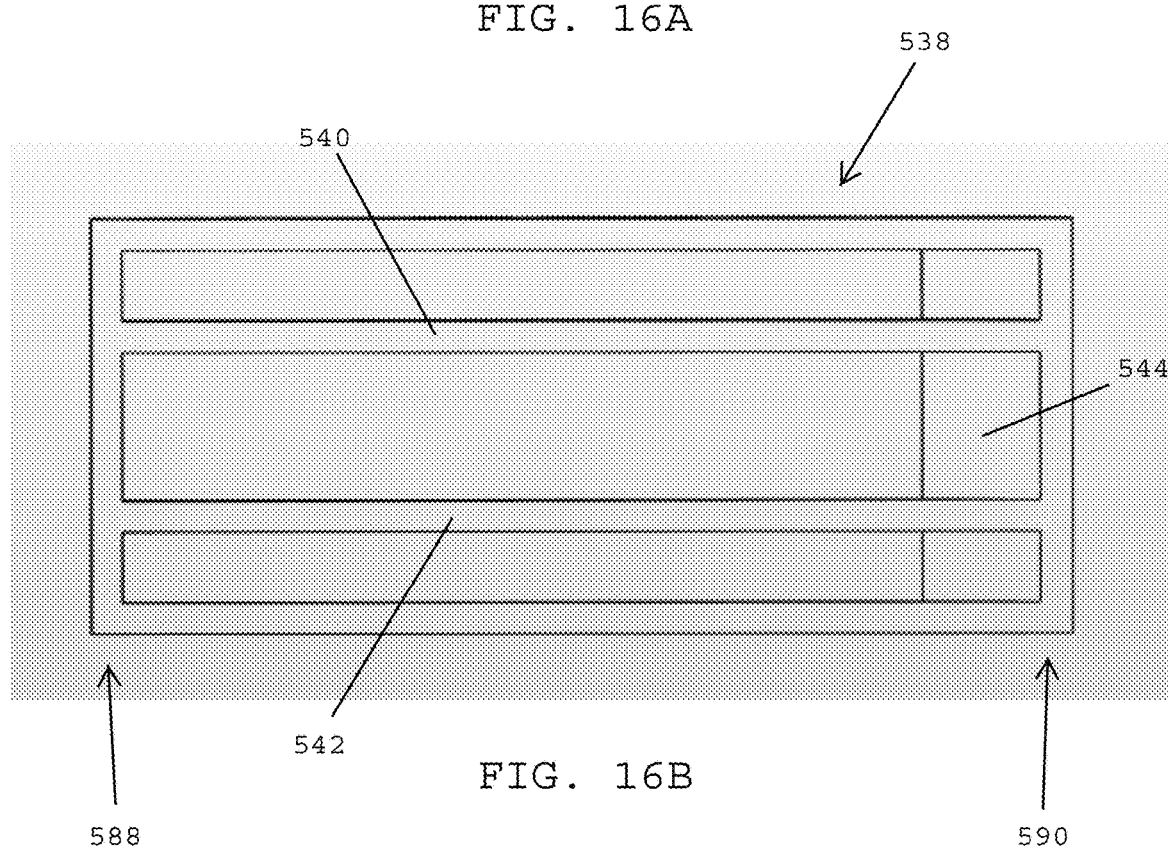
FIG. 16B is a top plan view of the needle driver alignment guide shown in FIG. 16A.

Referring to FIGS. 16A and 16B, a needle driver alignment guide 538 preferably has a first lateral guide wall 540 and an opposing second lateral guide wall 542 that extend from a proximal end 588 to a distal end 590 of the needle driver alignment guide. The needle driver alignment guide 538 preferably has a longitudinal axis $A_7$ that extends from the proximal end 588 to the distal end 590 of the needle driver alignment guide. The needle driver alignment guide 538 preferably includes an end wall 588 that extends between distal ends of the respective first and second lateral guide walls 540, 542. In one embodiment, the end wall 588 desirably functions as a hard stop for aligning the clamping jaws of a needle driver with a tip of a suture needle. The first and second lateral guide walls 540, 542 preferably define a needle driver guide channel that guides advancement of the jaws of a needle driver from the proximal end 588 to the distal end 590 of the needle driver alignment guide 538 so that the jaws may be properly aligned with a tip of a suture needle, as will be described in more detail herein.

Figure 17A:
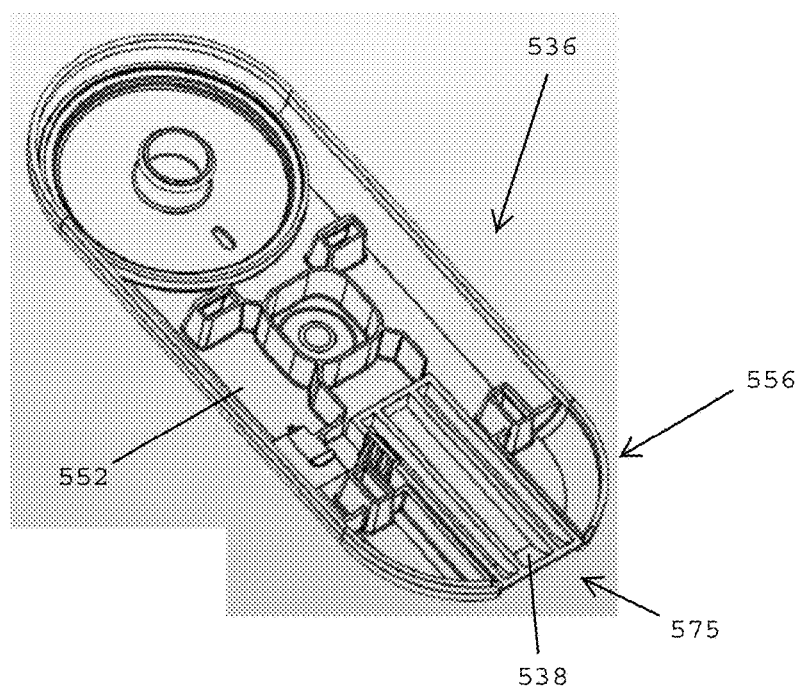
FIG. 17A is a perspective view of the base of FIGS. 15A-15B and the needle driver alignment guide of FIGS. 16A-16B assembled with the base, in accordance with one embodiment of the present patent application.
Figure 17B:
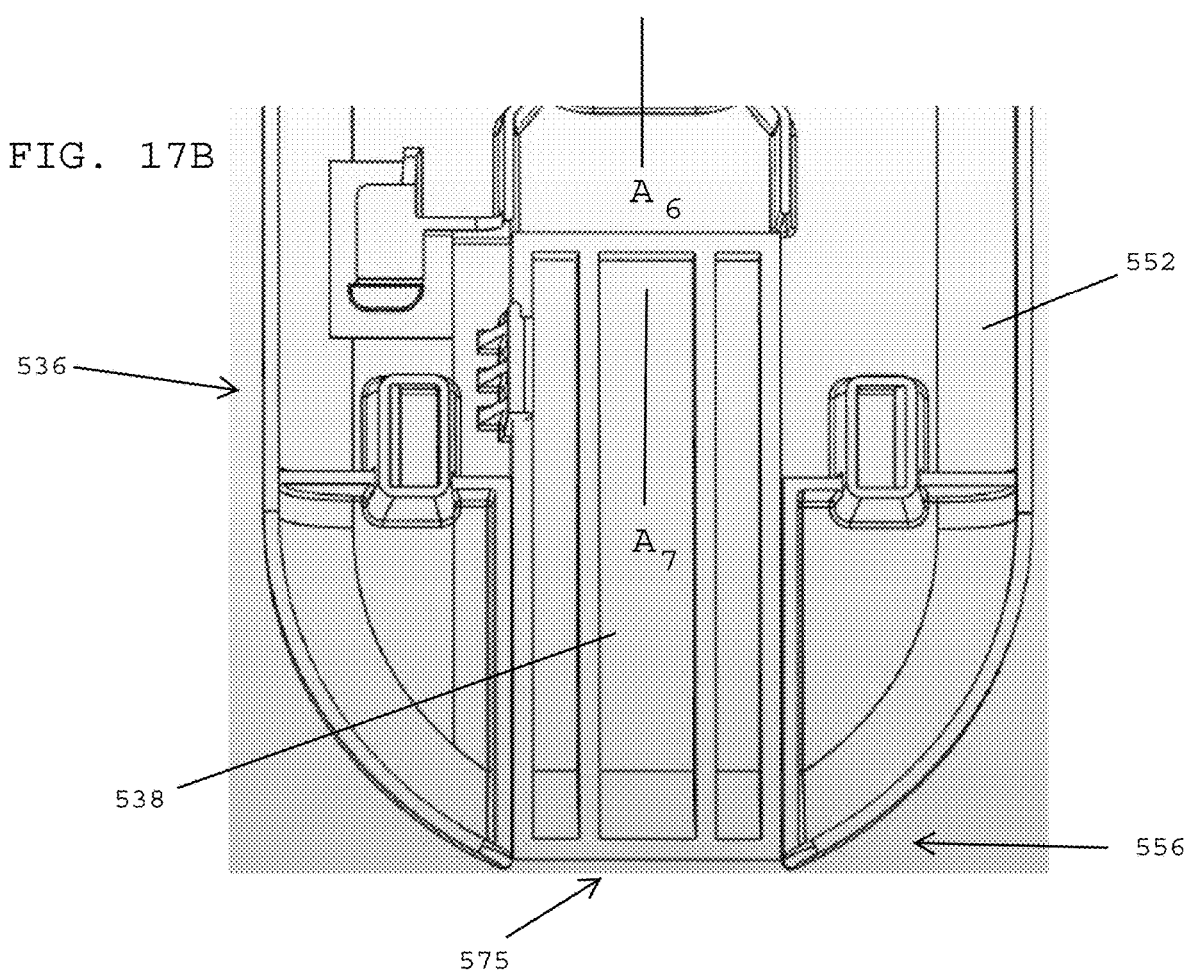
FIG. 17B shows a magnified view of a distal end of the base and the needle driver alignment guide shown in FIG. 17A.

Referring to FIGS. 17A and 17B, in one embodiment, the needle driver alignment guide 538 is preferably assembled with the base 552 by inserting the needle driver alignment guide into the gap 575 located at the distal end 556 of the base 552 of the suture needle package 536. The longitudinal axis $A_7$ of the needle driver alignment guide 538 preferably extends along the longitudinal axis $A_6$ of the base 552.

Figure 18A:
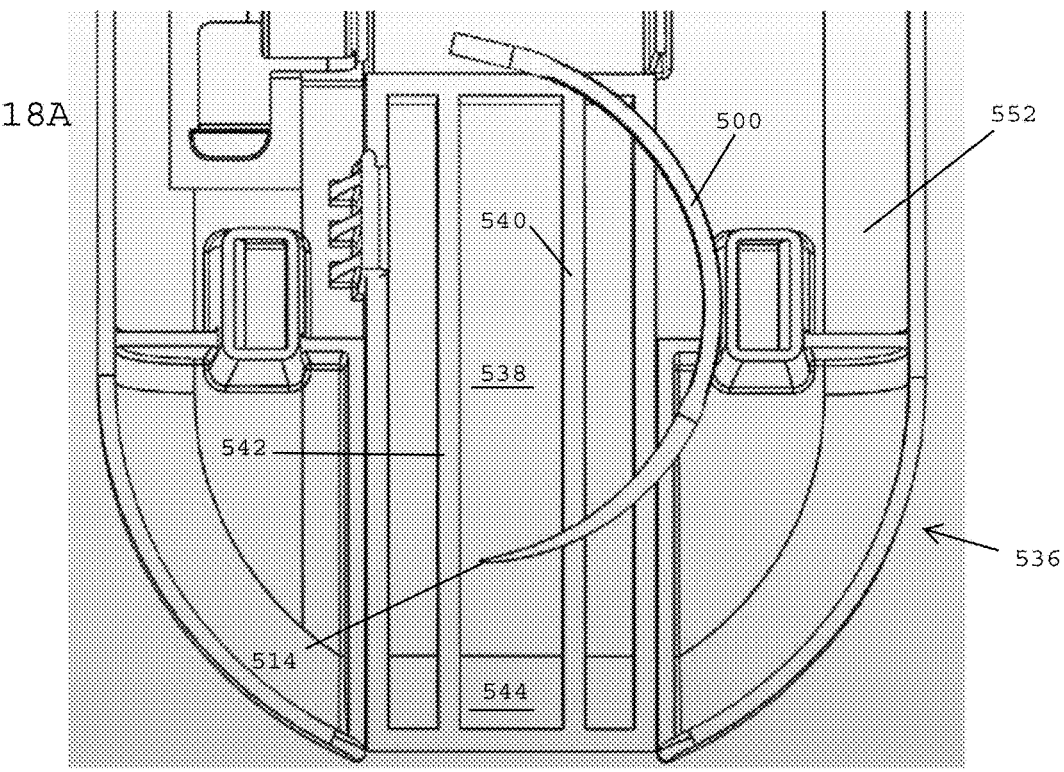
FIG. 18A is a top plan view of the distal end of the base and the needle driver alignment guide of FIG. 17B with a tip of a suture needle aligned with the needle driver alignment guide, in accordance with one embodiment of the present patent application.
Figure 18B:
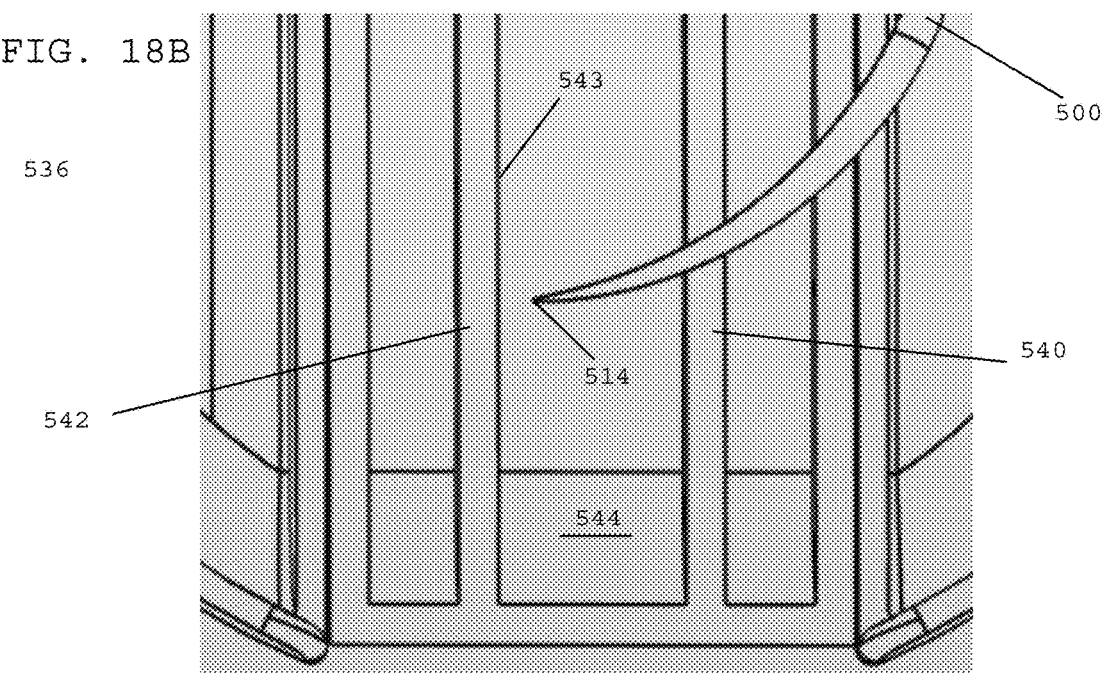
FIG. 18B is a magnified view of the tip of the suture needle and the needle driver alignment guide of FIG. 18A.

Referring to FIGS. 18A and 18B, in one embodiment, a suture needle 500 may be secured over the base 552 of the suture needle package 536 so that the tip 514 at the distalmost end of the suture needle 500 is located between the first and second lateral guide walls 540, 542 and is proximal to the end wall 544 of the needle driver alignment guide 538.

Referring to FIG. 18B, in one embodiment, the tip 514 is secured to the suture needle package 536 so that the tip 514 of the suture needle 500 is spaced away from the inner surface 543 of the second lateral guide wall 542. In addition, the tip 514 of the suture needle 500 is preferably located proximal to the end wall 544 of the needle driver alignment guide 538 so that a gap exists between the end wall 544 and the tip 514 of the suture needle 500.

Referring to FIGS. 19A-19F, in one embodiment, the needle driver 116 having the clamping assembly 124 located at the distal end 122 of the elongated shaft 118 may be utilized for removing the suture needle 500 from the suture needle package 536.

Figure 19A:
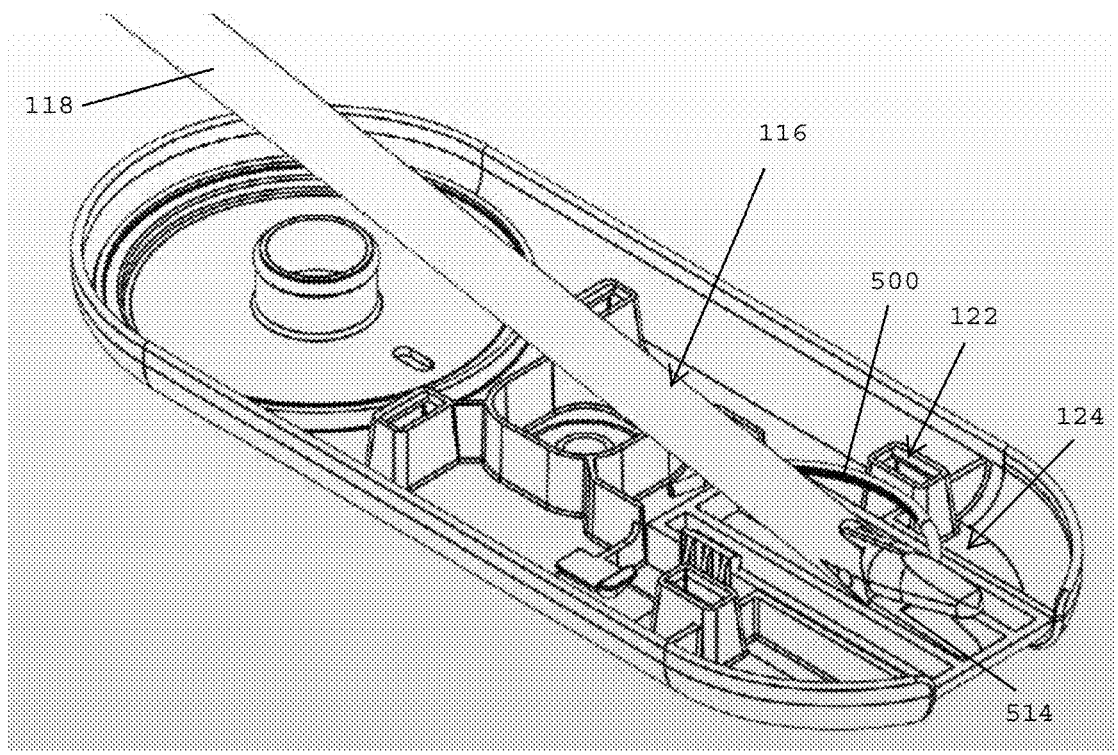
FIG. 19A is a perspective view of a method of using a needle driver to remove a suture needle from a suture needle package, in accordance with one embodiment of the present patent application.
Figure 19B:
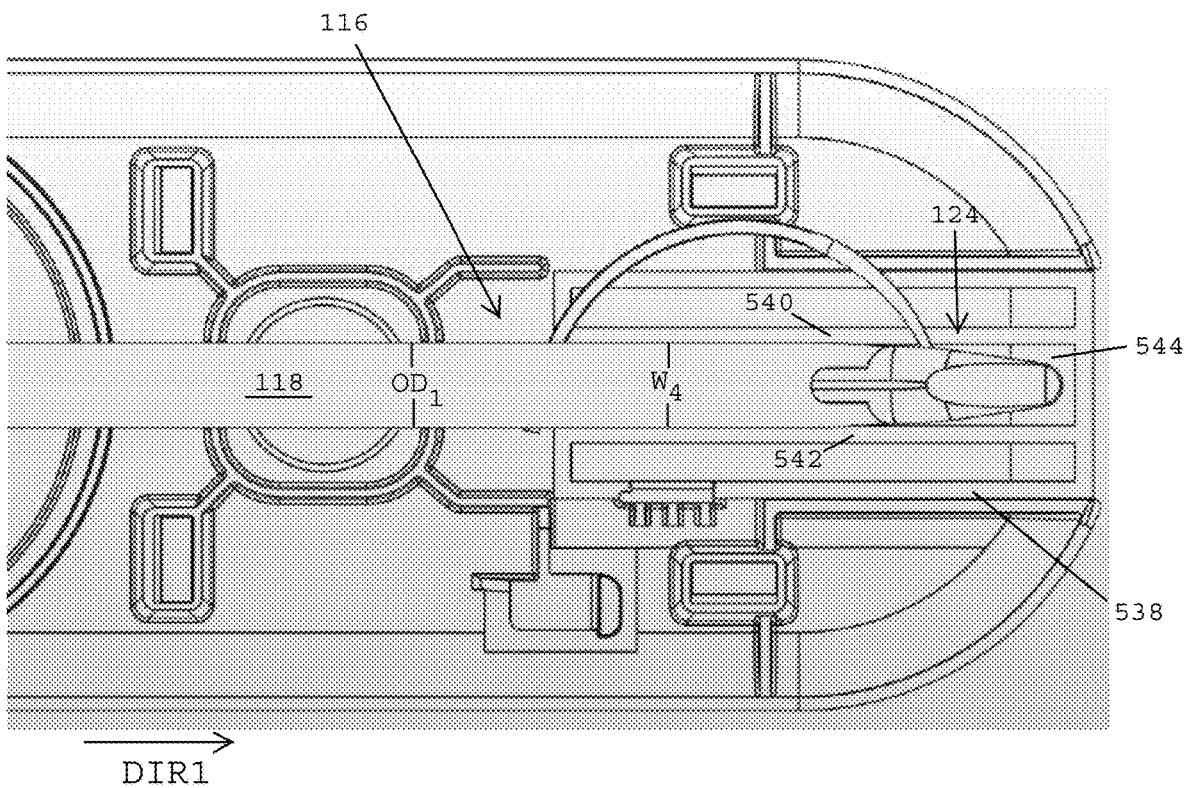
FIG. 19B is a top plan view of the needle driver, the suture needle package and the suture needle shown in FIG. 19A.
Figure 19C:
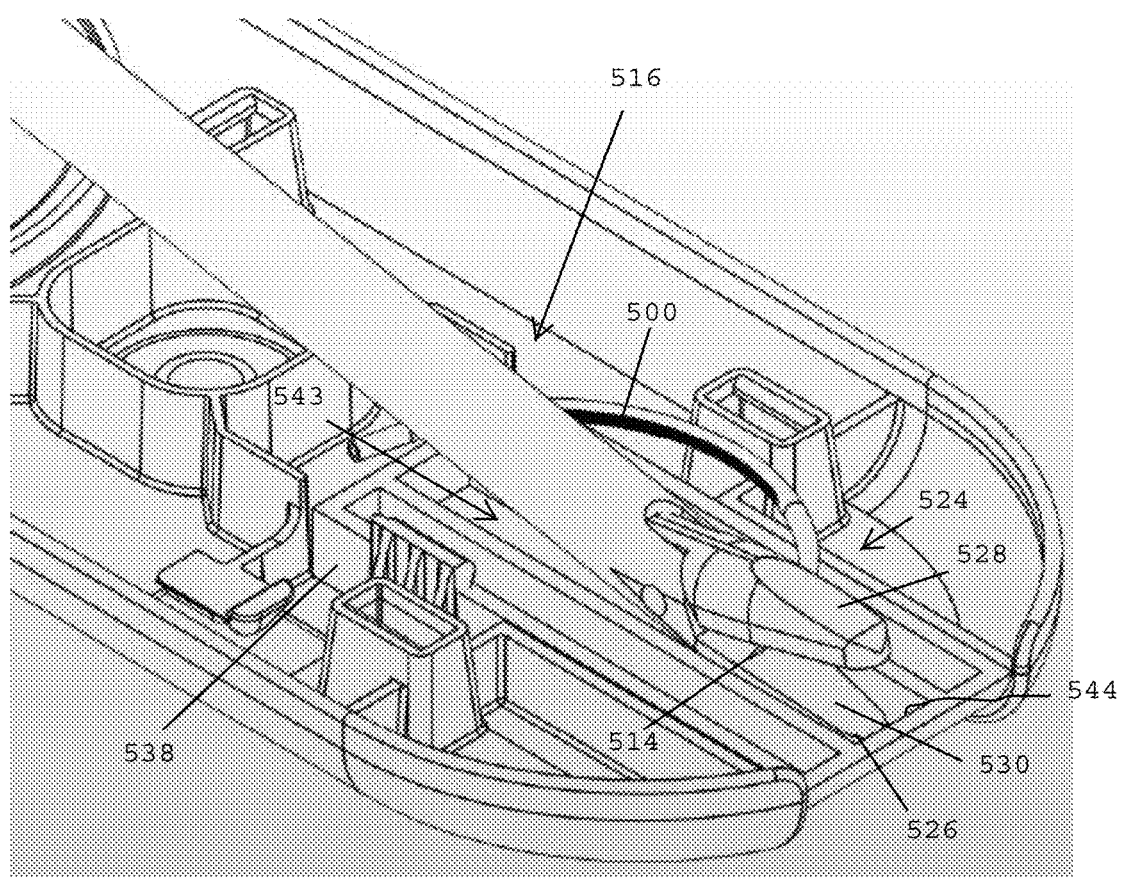
FIG. 19C is a perspective end view of the needle driver, the suture needle package and the suture needle shown in FIGS. 19A and 19B.
Figure 19D:
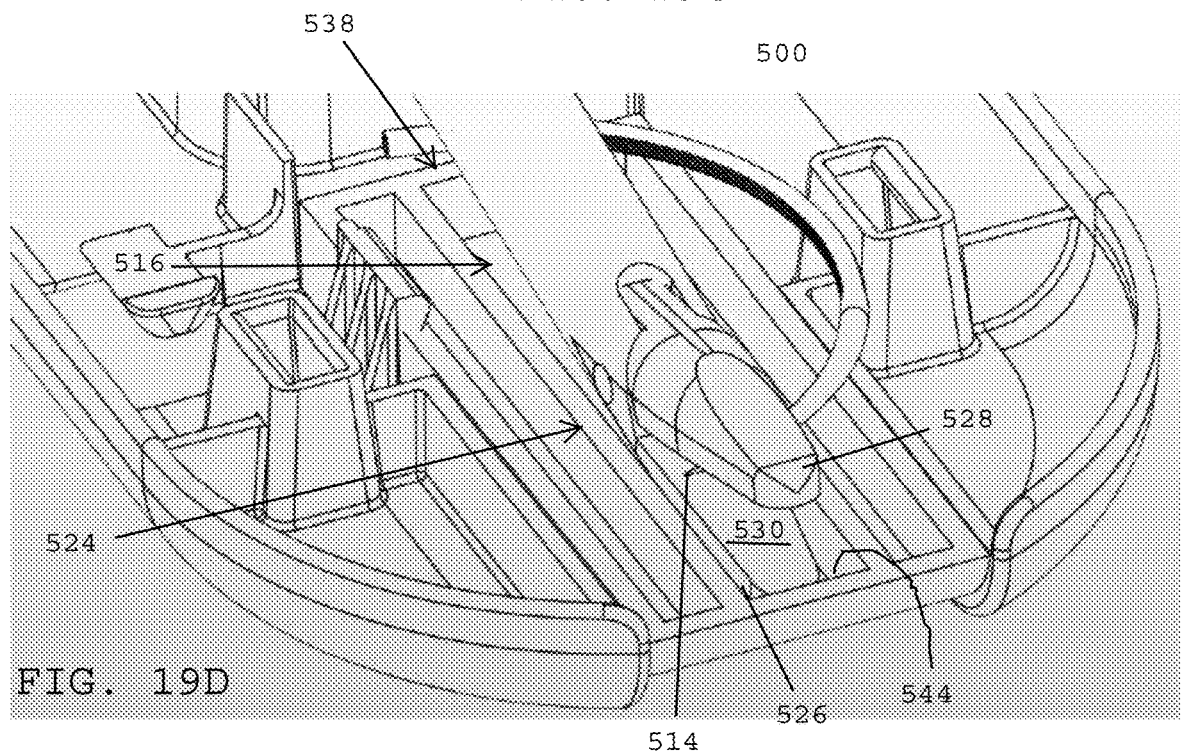
FIG. 19D is another perspective end view of the needle driver, the suture needle package and the suture needle shown in FIGS. 19A-19C.
Figure 19E:
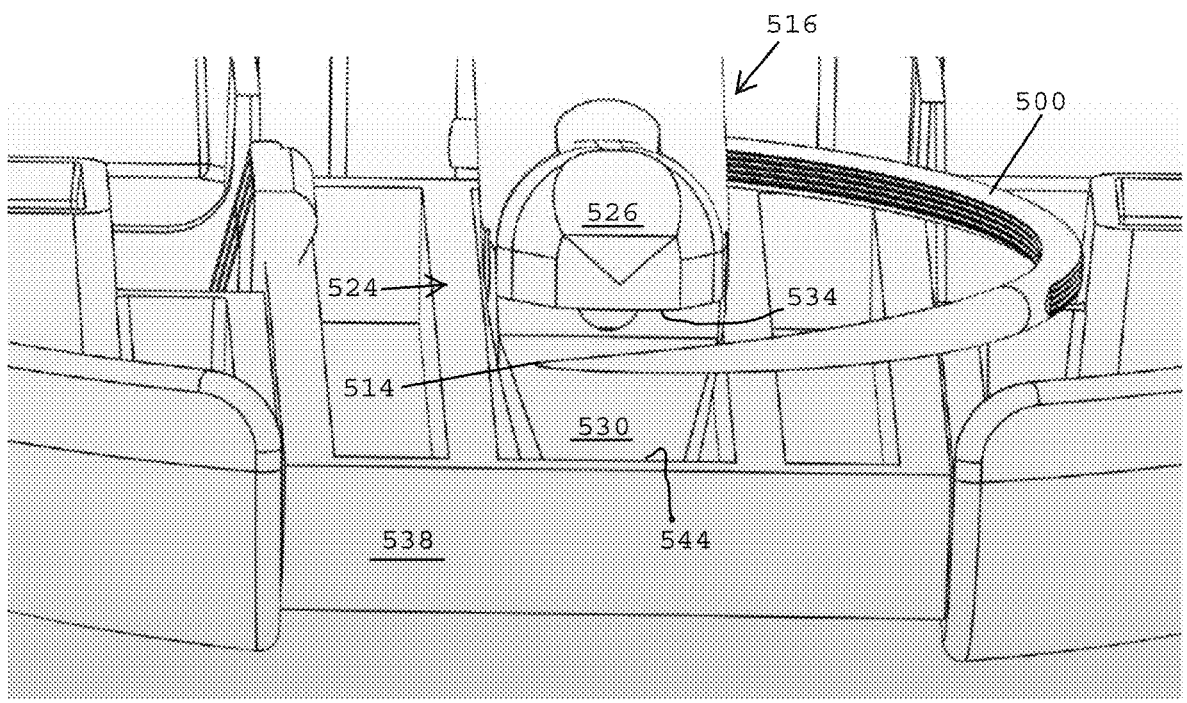
FIG. 19E is an end view of needle driver, the suture needle package and the suture needle shown in FIGS. 19A-19D.

Referring to FIG. 19B, in one embodiment, the elongated shaft 118 of the needle driver 116 has an outer diameter $OD_1$ that substantially matches the width $W_4$ of the guide channel that extends between the first lateral guide wall 540 and the second lateral guide wall 542 of the needle driver alignment guide 538. In one embodiment, the needle driver 116 is preferably advanced between the first and second lateral guide walls 540, 542 in the direction designated DIR1 until the distal end of the lower jaw of the clamping assembly 124 abuts against the end wall 544 of the needle driver alignment guide 538.

Figure 19F:
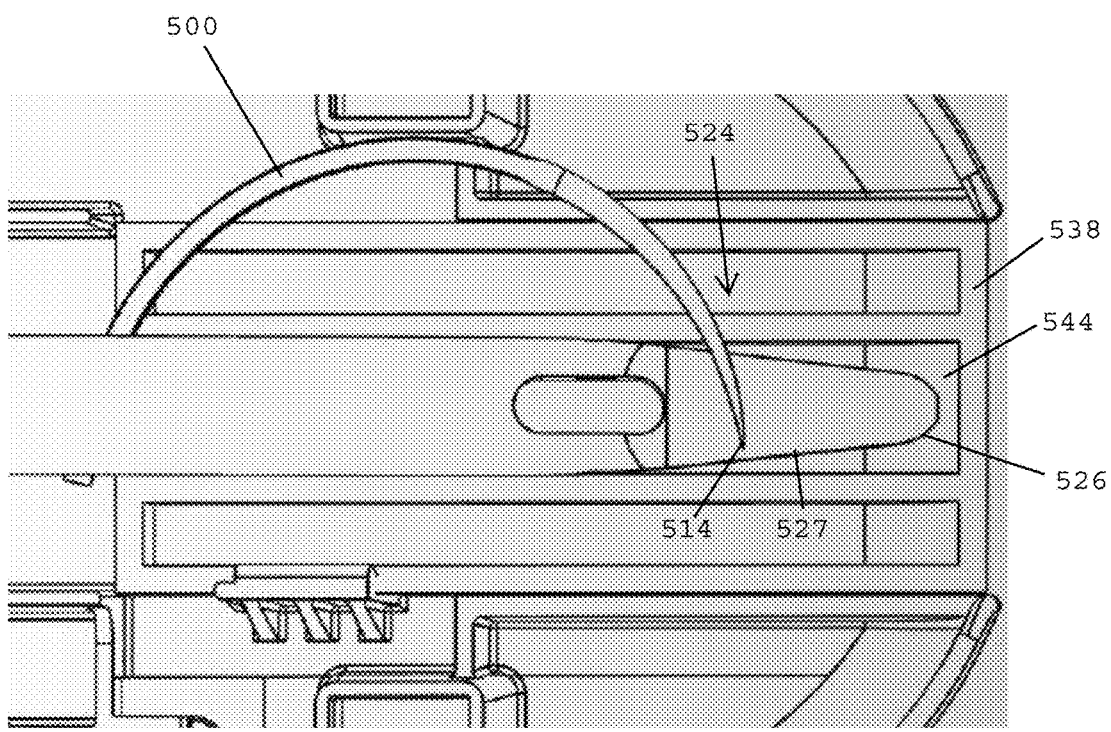
FIG. 19F is a top plan view of the needle driver, the suture needle package and the suture needle shown in FIGS. 19A-19E with an upper jaw of a clamping assembly removed to show the tip of the suture needle alignment with a top surface of a lower jaw, in accordance with one embodiment of the present patent application.

Referring to FIGS. 19C-19F, in one embodiment, when the lower jaw 526 of the clamping assembly 524 of the needle driver 516 has abutted against the end wall 544 of the needle driver alignment guide 538, the top and bottom surfaces 530, 534 of the respective lower and upper jaws 526, 528 are preferably aligned with the tip 514 of the suture needle 500. The top and bottom surfaces 530, 534 of the opposing jaws 526, 528 desirably have respective lengths that are greater than the distance between the tip 514 of the suture needle and the end wall 544 of the needle driver alignment guide 538 so that the tip 514 of the suture needle is located between the proximal and distal ends of the clamping surfaces and inside the lateral boundaries of the lower and upper jaws. As shown in FIG. 19F, the tip 514 of the suture needle 500 is positioned inside the lateral wall 527 of the lower jaw 526 and is spaced proximally from the end wall 544 so that the tip 514 of the suture needle 500 is not exposed and does not extend outside the perimeter of the lower and upper jaws of the clamping assembly 524. As a result, the tip 514 is protected and surrounded by the lower and upper jaws as the needle driver pulls the suture needle 500 through a trocar for positioning the suture needle at a surgical site.

Referring to FIG. 20A, in one embodiment, the needle driver alignment guide 538 has a first lateral guide wall 540 having a lower end 545 and an upper end 555 that define a depth $D_1$ of the needle driver alignment guide. The upper end 555 of the first lateral guide wall 540 has a securing notch 565 formed therein for securing a tapered section of the suture needle so that the tip 514 (FIG. 19F) of the suture needle is located in the needle driver guide channel of the needle driver alignment guide 538. The securing notch 565 spaces the tip 514 of the suture needle proximal to the end wall 544 of the needle driver alignment guide by a distance $L_6$.

Referring to FIGS. 20A and 20B, in one embodiment, the distal end of the needle driver 516 may be advanced distally in the direction DIR1 until the distal end of the lower jaw 526 of the clamping assembly 524 engages the end wall 544 (FIG. 20B), which preferably provides tactile feedback to a surgeon that the clamping assembly has reached the end of the needle driver guide channel and is aligned with the tip 514 of the suture needle.

Referring to FIG. 20B, when the distal end of the lower jaw 526 engages the end wall 544 of the needle driver guide channel 538, the top surface 530 of the lower jaw 526 is preferably aligned with the tip 514 of the suture needle. The top surface 530 of the lower jaw 526 preferably has a length $L_7$ that is greater than the distance $L_6$ between the tip 514 of the suture needle and the end wall 544 of the needle driver alignment guide 538 so that the tip is positioned between the proximal and distal ends of the top surface 530 of the lower jaw 526. The bottom surface 534 of the upper jaw 528 preferably has a similar length as the top surface of the lower jaw. In one embodiment, the securing notch 565 holds the tip 514 at a known height that is between the lower end 545 and the upper end 555 of the first lateral guide wall 540 so that the top surface 530 of the lower jaw 526 is positioned under the tip 514 of the suture needle and the bottom surface 534 of the upper jaw 528 is positioned over the tip 514 of the suture needle. The suture needle package may be designed so that the tip of the suture needle is held at a predetermined location having known X, Y, and Z coordinates. The needle driver alignment guide and the needle driver may be designed to have dimensions to insure that the clamping surfaces of the needle driver jaw may be consistently and repeatedly aligned with the tip to ensure that the tip is protected and surrounded by the clamping assembly as the suture needle is passed through a trocar.

Figure 21:
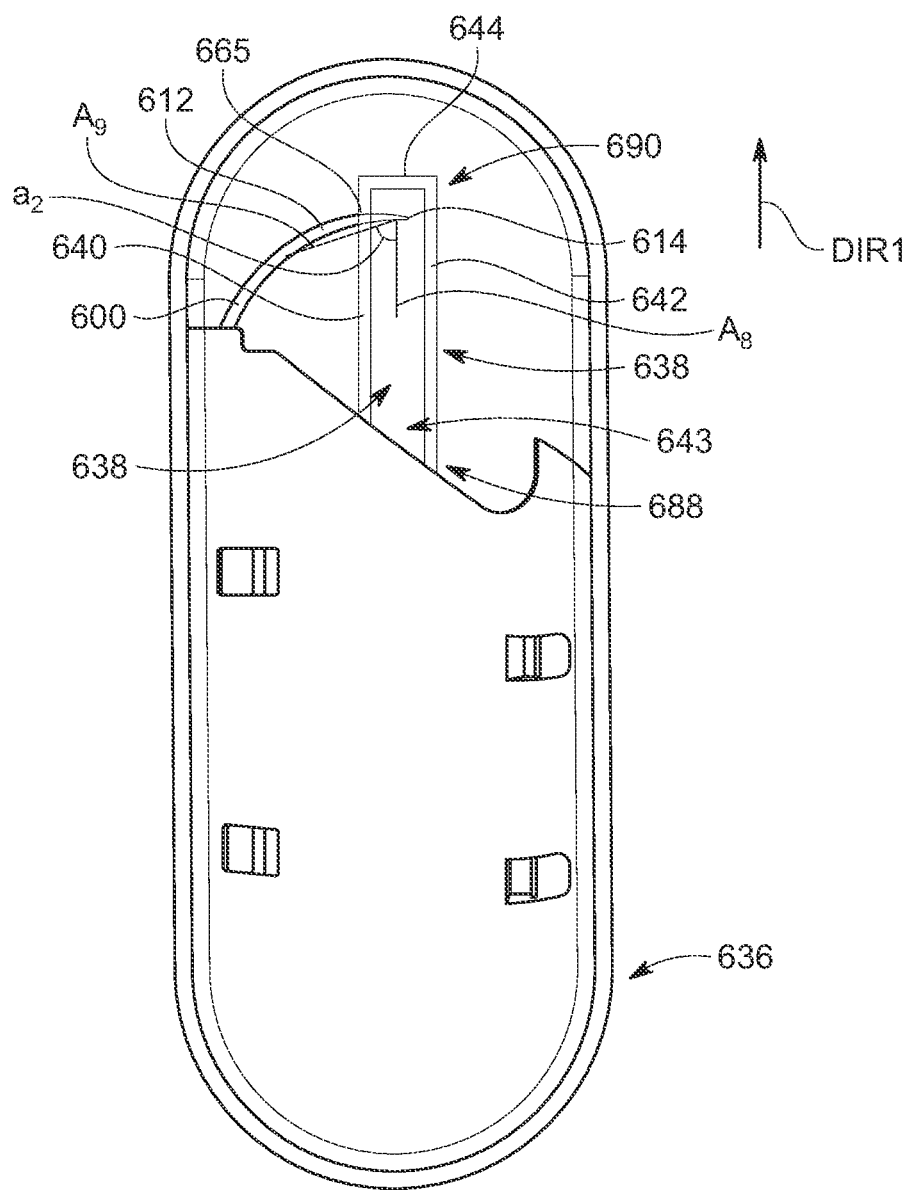
FIG. 21 shows a top plan view of a suture needle package having a needle driver alignment guide and a tip of a suture needle positioned within the needle driver alignment guide, in accordance with one embodiment of the present patent application.

Referring to FIG. 21, in one embodiment, a suture needle package 636 preferably includes a needle driver alignment guide 638 that extends along a longitudinal axis $A_8$. The needle driver alignment guide 638 preferably includes a first lateral guide wall 640, an opposing second lateral guide wall 642, and an end wall 644 that interconnects distal ends of the first and second lateral guide wall 640, 642. The first and second lateral guide wall 640, 642 and the end wall 644 preferably define a needle driver guide channel 643 that is configured to guide a needle driver so that the clamping jaws of the needle driver are aligned with the tip 614 of the suture needle 600.

In one embodiment, the suture needle package 636 preferably includes a releasable connector 665 that secures a tapered section 612 of the suture needle 600 to the suture package so that the tip 614 is located within the elongated channel of the needle driver alignment guide 638. The connector 665 preferably holds the suture needle 600 at a preferred orientation relative to the longitudinal axis $A_8$ so that the tapered section 612 of the suture needle extends along an axis $A_9$ that defines an angle $\alpha_2$ of less than 90 degrees relative to the axis $A_8$, which will require less force for passing the suture needle through a trocar. In one embodiment, the jaws of a needle driver may be inserted into the slot at the proximal end 688 of the needle driver alignment guide 638 and advanced in the direction DIR1 toward the end wall 644 at the distal end of the needle driver alignment guide 638. Once at least one of the jaws (e.g., the lower jaw) abuts against the end wall 644, the opposing top and bottom surfaces of the respective lower and upper jaws are preferably aligned with the tip 614 of the suture needle 600. The jaws may be closed for clamping the tapered section and the tip 614 between the opposing jaws. Once the clamping assembly has been closed for clamping onto the tapered section 612 of the suture needle 600, the needle driver may be lifted away from the suture package 636 to remove the suture needle from the suture package.

Figure 22:
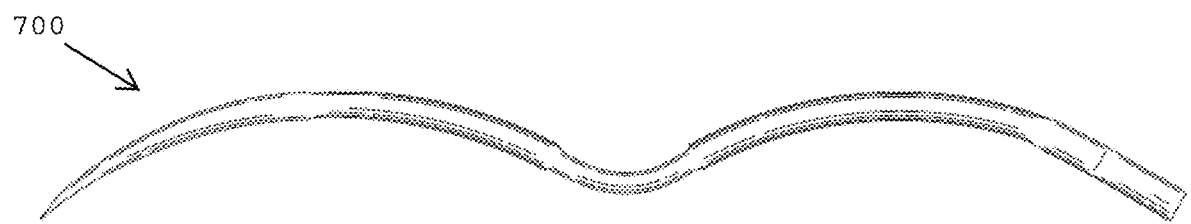
FIG. 22 shows a side view of a suture needle having a bendable region for bending the suture needle into a seagull shaped configuration, in accordance with one embodiment of the present patent application.
Figure 23:
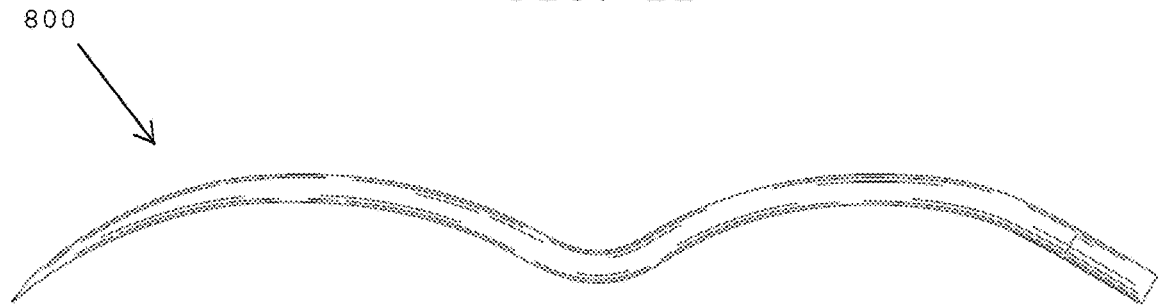
FIG. 23 shows a side view of a suture needle having a bendable region for bending the suture needle into a seagull shaped configuration, in accordance with one embodiment of the present patent application.
Figures 24, 25:
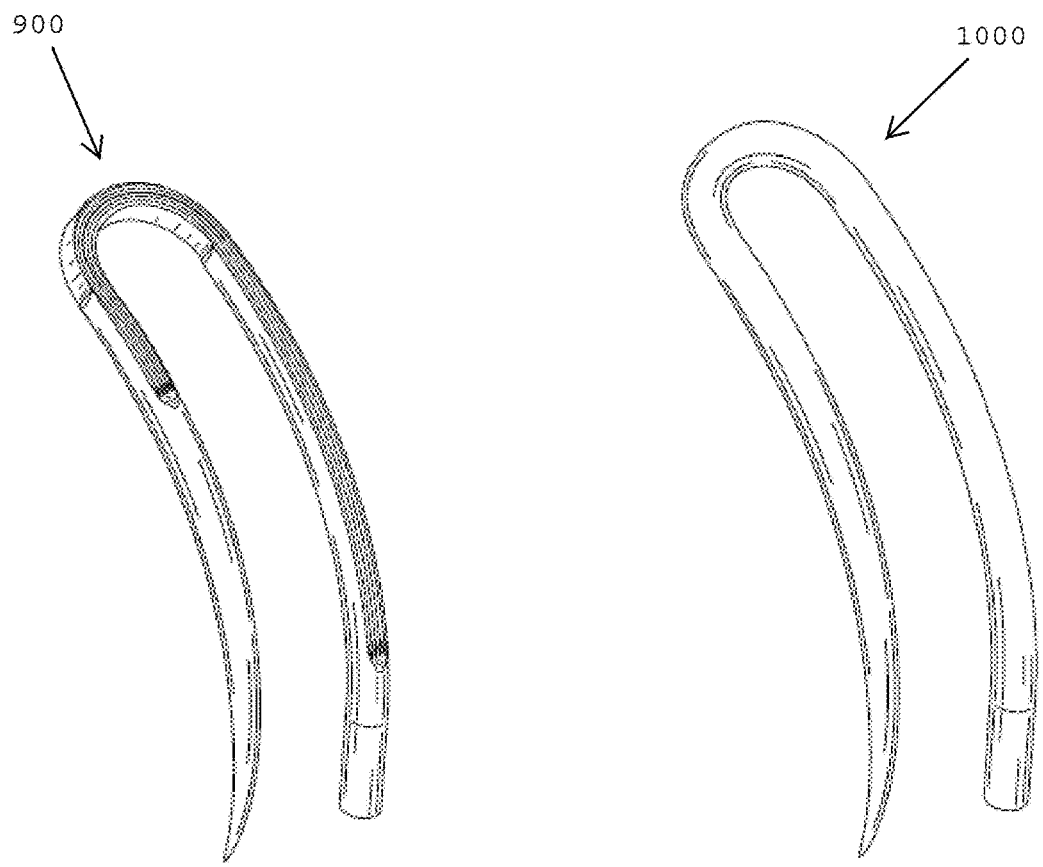
FIG. 24 shows a side view of a suture needle having a bendable region for folding the suture needle in half so that the tip is adjacent the proximal end of the suture needle, in accordance with one embodiment of the present patent application.
FIG. 25 shows a side view of a suture needle having a bendable region for folding the suture needle in half do that the tip is adjacent the proximal end of the suture needle, in accordance with one embodiment of the present patent application.

In one embodiment, the systems, suture packages, devices and methods disclosed herein may be used for passing suture needles having bendable or foldable regions through smaller trocars, whereby the suture needles are bent or folded to reduce their outer dimensions, heights, and/or profiles for being passed through trocars (e.g., a 5 mm trocar), as disclosed in commonly assigned U.S. patent application Ser. No. 16/282,604, filed on Feb. 22, 2019, published as U.S. 2020/0268378 , Ser. No. 16/282,652, filed on Feb. 22, 2019, published as U.S. 2020/0268379, and Ser. No. 16/781,055, filed on Feb. 4, 2020, which benefit of U.S. Provisional Application Number 62/809,016, filed on Feb. 22, 2019, and now published as U.S. 2020/0268380, the disclosures of which are hereby incorporated by reference herein. Referring to FIGS. 22 and 23, in one or more embodiments, suture needles 700, 800 have bendable regions that enable the needles to be bent into seagull shaped configurations for being passed through smaller trocars. Referring to FIGS. 24 and 25, in one embodiment, suture needles 900, 1000 have bendable regions that enable the needles to be folded in half so that the tips of the needles are adjacent the proximal ends of the needles for being passed through smaller trocars. After being passed through trocars using the suture needle packages, needle driver guide channels, and needle drivers disclosed herein, the suture needles may be bent into a curved configuration (e.g., a half circle) for use in a suturing operation. At the conclusion of the suturing operation, the suture needles may be bent back into the configurations shown in FIGS. 22-25 for withdrawing the suture needles from the trocars.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A suture needle package comprising:
a base;
a needle driver alignment guide overlying said base, said needle driver alignment guide including first and second lateral guide walls that oppose one another for defining a needle driver guide channel;
a suture needle overlying said base, said suture needle including a proximal end and a distal end having a tapered section that terminates at a tip, said suture needle having a mid-section that is located between said proximal and distal ends of said suture needle;
at least one connector releasably securing said suture needle over said base, wherein said at least one connector orients said suture needle relative to said first and second lateral guide walls so that said tip of said suture needle is located within said needle driver guide channel and is bounded by said first and second lateral guide walls and so that said mid-section of said suture needle is located outside of said needle driver guide channel and said needle driver alignment guide.

2. The suture needle package as claimed in claim 1, wherein said needle driver guide channel has a proximal end, a distal end, and a longitudinal axis that extends between said proximal and distal ends thereof.

3. The suture needle package as claimed in claim 2, wherein said needle driver alignment guide further comprises an end wall interconnecting said first and second lateral guide walls for defining said distal end of said needle driver guide channel.

4. The suture needle package as claimed in claim 3, wherein said end wall interconnects distal ends of said first and second lateral guide walls, and wherein said first and second lateral guide walls are parallel to one another.

5. The suture needle package as claimed in claim 4, wherein said end wall and said distal ends of said first and second lateral side walls surround said tip of said suture needle.

6. The suture needle package as claimed in claim 5, wherein each of said first and second lateral guide walls has a lower end and an upper free end, and wherein said at least one connector holds said tip of said suture needle between said lower ends and said upper free ends of said respective first and second lateral guide walls.

7. The suture needle package as claimed in claim 6, wherein said at least one connector secures said tip of said suture needle closer to said distal end of said needle driver guide channel and secures said proximal end of said suture needle closer to said proximal end of said needle driver guide channel.

8. The suture needle package as claimed in claim 7, wherein said at least one connector comprises a securing notch formed in said upper free end of one of said first and second lateral guide walls, and wherein said tapered section of said suture needle is seated in said securing notch and extends proximally from said tip of said suture needle.

9. The suture needle package as claimed in claim 8, wherein said tapered section of said suture needle extends along an axis that defines an angle with said longitudinal axis of said needle driver alignment channel of less than 90 degrees.

10. The suture needle package as claimed in claim 9, wherein said at least one connector further comprises a second connector that is located proximal to said securing notch for securing a section of said suture needle that is proximal to said tapered section of said suture needle.

11. The suture needle package as claimed in claim 1, wherein said suture needle comprises a superelastic alloy.

12. A system for aligning a needle driver with a tip of a suture needle comprising:
   a suture needle package having a base, a needle driver alignment guide overlying said base, and at least one connector for releasably securing a suture needle to said suture needle package;
   said needle driver alignment guide including first and second lateral guide walls that oppose one another for defining a needle driver guide channel;
   an end wall interconnecting said first and second lateral guide walls for defining a distal end of said needle driver alignment guide;
   said suture needle overlying said base, said suture needle including a proximal end and a distal end having a tapered section that terminates at a tip, said suture needle having a mid-section that is located between said proximal and distal ends of said suture needle;
   said at least one connector securing said suture needle over said base and controlling the orientation of said suture needle so that said tip of said suture needle is located within said needle driver guide channel and is bounded by said end wall and said first and second lateral guide walls and so that said mid-section of said suture needle is located outside of said needle driver guide channel and said needle drive alignment guide;
   a needle driver comprising an elongated shaft and a clamping assembly located at a distal end of said elongated shaft, wherein said clamping assembly engages said end wall of said needle driver alignment guide for aligning said clamping assembly with said tip of said suture needle.

13. The system as claimed in claim 12, wherein said at least one connector holds said tip of said suture needle between said first and second lateral guide walls so that said tip is spaced away from said first and second lateral guide walls.

14. The system as claimed in claim 13, wherein said at least one connector holds said tip of said suture needle proximal to and spaced away from said end wall of said needle driver alignment guide by a first distance.

15. The system as claimed in claim 14, wherein said clamping assembly has a lower jaw with a top surface and an opposing upper jaw with a bottom surface that is pivotally coupled with said lower jaw for moving said clamping assembly between open and closed positions, wherein a distal end of said lower jaw engages said end wall, and wherein said top surface of said lower jaw is aligned with said tip of said suture needle.

16. The system as claimed in claim 15, wherein said top surface of said lower jaw has a length that extends between a proximal end and said distal end thereof, and wherein said length of said top surface of said lower jaw is greater than said first distance between said tip of said suture needle and said end wall of said needle driver alignment guide.

17. The system as claimed in claim 16, wherein said upper jaw of said damping assembly is positioned over said tip of said suture needle and said lower jaw of said damping assembly is positioned under said tip of said suture needle.

18. The system as claimed in claim 17, wherein said first and second lateral guide walls are spaced from one another to define a width of said needle driver alignment guide that extends from said first lateral guide wall to said second lateral guide wall.

19. The system as claimed in claim 17, wherein said elongated shaft of said needle driver has a width that is substantially equal to said width of said needle driver alignment guide.

20. The system as claimed in claim 17, further comprising a resilient element disposed between said first and second lateral guide walls for urging said needle driver against one of said first and second lateral guide walls.

21. The system as claimed in claim 12, wherein said elongated shaft of said needle driver has an outer diameter, and wherein said needle driver alignment guide has a depth that is about ½ the dimension of said outer diameter of said elongated shaft of said needle driver.

22. A method of delivering a suture needle to a surgical site comprising:
   obtaining a suture needle package having a needle driver alignment channel, and a suture needle secured to said suture needle package, said suture needle having a distal end with a tapered section that terminates at a tip, wherein said tapered section and said tip of said suture needle are positioned within said needle driver alignment channel;
   positioning a needle driver in said needle driver alignment channel, said needle driver having a clamping assembly at a distal end thereof, said clamping assembly including a lower jaw and an opposing upper jaw that are moveable between open and closed positions;
   with said clamping assembly of said needle driver in the open position, advancing said clamping assembly along a longitudinal axis of said needle driver alignment channel toward a distal end of said needle driver alignment channel for aligning said clamping assembly with said tip of said suture needle whereupon the entirety of said lower jaw of said clamping assembly is positioned below said tip of said suture needle and said upper jaw of said clamping assembly is positioned above said tip of said suture needle;
   moving said clamping assembly to said closed position for clamping said portion of said tapered section of said suture needle that is positioned within said needle driver alignment channel, wherein said closed clamping assembly covers said tip with said tip being positioned between an upper surface of said lower jaw and a lower surface of said upper jaw for preventing exposure of said tip outside said clamping assembly;
using said closed clamping assembly for lifting said suture needle out of said suture needle package.

23. The method as claimed in claim 22, with said proximal end of said suture needle trailing said tip of said suture needle, using said closed clamping assembly for passing said suture needle through a trocar.

24. The method as claimed in claim 23, wherein said suture needle is made of a superelastic material, wherein said suture needle has a more curved configuration when secured to said suture needle package and a less curved configuration during passing said suture needle through said trocar.

* * * * *